US009173355B2

(12) United States Patent
Maxwell

(10) Patent No.: US 9,173,355 B2
(45) Date of Patent: Nov. 3, 2015

(54) CARROTS HAVING INCREASED LYCOPENE CONTENT

(75) Inventor: Robert V. Maxwell, Payette, ID (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 1316 days.

(21) Appl. No.: 11/874,629

(22) Filed: Oct. 18, 2007

(65) Prior Publication Data
US 2008/0098493 A1 Apr. 24, 2008

Related U.S. Application Data

(60) Provisional application No. 60/852,397, filed on Oct. 18, 2006, provisional application No. 60/905,809, filed on Mar. 9, 2007.

(51) Int. Cl.
A01H 5/06 (2006.01)
(52) U.S. Cl.
CPC ........................................ A01H 5/06 (2013.01)
(58) Field of Classification Search
CPC ........................................................ A01H 5/06
USPC ........................................................ 800/298
See application file for complete search history.

(56) References Cited

U.S. PATENT DOCUMENTS

| 6,787,685 B2 | 9/2004 | Maxwell | 800/298 |
|---|---|---|---|
| 8,217,229 B2 | 7/2012 | Maxwell | |
| 2003/0154519 A1 | 8/2003 | Maxwell | 800/295 |

FOREIGN PATENT DOCUMENTS

| JP | A-09-107760 | 4/1997 |
|---|---|---|
| JP | 11-151034 | 6/1999 |
| JP | JP 11-151034 | 6/1999 |
| JP | A-2002-272233 | 9/2002 |
| JP | A-2005-501541 | 1/2005 |
| JP | A-2005-315877 | 11/2005 |
| JP | A-2006-020558 | 1/2006 |
| JP | 2007-014205 | 1/2007 |
| WO | WO 03/020053 | 3/2003 |

OTHER PUBLICATIONS

Chen et al. 1999. Molecular Breeding 5: 283-299.*
Gillespie et al. 1989. Genetics 121: 129-138.*
Mayer-Miebach et al. 2005. Food Research International 38: 1103-1108.*
Harrill. 1998. Perfect Blend Organics, 'Using a refractometer to test the quality of fruits and vegetables'.*
Mayer-Miebach et al. Food Research International 38: 1103-1108, 2005.*
Stein et al. Plant Breeding 114: 1-11, 1995.*
Smith. 2001 Grant project final report, Department of Agriculture, Trade and Consumer Protection, Division of Agricultural Development, pp. 1-10, 2002.*
PVP 9900093, 'BetaKing' 2001.*
Chen et al. Molecular Breeding 5: 283-299, 1999.*
Gillespie et al. Genetics 121: 129-138, 1989.*
"New rainbow carrots revive ancient colors," Seminis Vegetable Seeds, Inc., News Release, Oxnard, California, May 19, 2004.
Buishand et al., "Studies on the inheritance of root color and carotenoid content in red x yellow and red x white crosses of carrot, Daucus carota L.," Euphytica, 29(2):241-260, 1980.
Gills et al., "Sensory profiles of carrot (Daucus carota L.) cultivars grown in Georgia," HortScience, 34(4):625-628, 1999.
Nyman et al., "Effects of cultivar, root weight, storage and boiling on carbohydrate content in carrots (Daucus carota L)," J. Sci. Food Agri., 85:441-449, 2004.
PVP Application for Carrot (Daucus carota) Variety 0710 0303, undated.
PVP Application for Carrot (Daucus carota) Variety 0710 0304, undated.
PVP Application for Carrot (Daucus carota) Variety 0710 0305, undated.
PVP Application for Carrot (Daucus carota) Variety 0710 0310, undated.
PVP Application for Carrot (Daucus carota) Variety 0710 0311, undated.
PVP Application for Carrot (Daucus carota) Variety 0710 0313, undated.
PVP Application for Carrot (Daucus carota) Variety 0710 0316, undated.
PVP Application for Carrot (Daucus carota) Variety 0710 0319, undated.
PVP Application for Carrot (Daucus carota) Variety 0710 0325, undated.
PVP Application for Carrot (Daucus carota) Variety RF 71-4911A, undated.
PVP Application for Carrot (Daucus carota) Variety RF 71-4912A, undated.
PVP Application for Carrot (Daucus carota) Variety RIF 71-4966C, undated.
PVP Application for Carrot (Daucus carota) Variety RIF 71-4967B, undated.
PVP Application for Carrot (Daucus carota) Variety RIF 71-4968B, undated.

(Continued)

Primary Examiner — Keith O. Robinson
(74) Attorney, Agent, or Firm — Dentons US LLP; Alissa Eagle Esq.

(57) ABSTRACT

The present invention relates to carrot lines having roots containing increased levels of lycopene, as well as containers of such carrots. The present invention also relates to parts of carrot plants from lines having roots with increased lycopene content, including seeds capable of growing carrot plants with increased root lycopene content. The invention also provides seed and plants of the carrot lines designated RN 71-4904C, RF 71-4911A, RF 71-4912A, RIF 71-4966C, RIF 71-4967B, or RIF 71-4968B. The invention thus relates to the plants, seeds and tissue cultures of carrot line RN 71-4904C, RF 71-4911A, RF 71-4912A, RIF 71-4966C, RIF 71-4967B, or RIF 71-4968B, and to methods for producing a carrot plant produced by crossing a plant of carrot line RN 71-4904C, RF 71-4911A, RF 71-4912A, RIF 71-4966C, RIF 71-4967B, or RIF 71-4968B with itself or with another carrot plant, such as a plant of another line. The invention further relates to seeds and plants produced by such crossing. The invention further relates to parts of a plant of carrot line RN 71-4904C, RF 71-4911A, RF 71-4912A, RIF 71-4966C, RIF 71-4967B, or RIF 71-4968B, including the fruit and gametes of such plants.

15 Claims, No Drawings

(56) References Cited

OTHER PUBLICATIONS

PVP Application for Carrot (*Daucus carota*) Variety RN 71-4904C, undated.
PVP Application for Carrot (*Daucus carota*) Variety RN 71-4963C, undated.
Santos et al, "QTL analyses reveal clustered loci for accumulation of major provitamin A carotenes and lycopene in carrot roots," *Mol. Genet. Genomics*, 268:122-129, 2002.
Seljasen et al., "Sensory and chemical changes in five varieties of carrot (*Daucus carota* L.) in response to mechanical stress at harvest and post-harvest," *J. Sci. Food Agric.*, 81:436-447, 2001.
Smith, "Commercial production of new carrot cultivars for the specialty juice industry—2001 Grant project final report," Department of Agriculture, Trade and Consumer Protection, Division of Agricultural Development, pp. 1-10, 2002.
Sood et al., "Carbohydrates and pigment assays in forty one genotypes of carrot (*Daucus carota* L.)," *J. Food Sci. Technol.*, 30(2):145-147, 1993.
Surles et al., "Carotenoid profiles and consumer sensory evaluation of specialty carrots (*Daucus carota*, L.) of various colors," *J. Agric. Food Chem.*, 52:3417-3421, 2004.
PVP Application for Carrot (*Daucus carota*) Variety RF 71-4911A, Jun. 4, 2008.
PVP Application for Carrot (*Daucus carota*) Variety RF 71-4912A, Jun. 4, 2008.
PVP Application for Carrot (*Daucus carota*) Variety RIF 71-4966C, Jun. 4, 2008.
PVP Application for Carrot (*Daucus carota*) Variety RN 71-4904C, Jun. 4, 2008.
PVP Application for Carrot (*Daucus carota*) Variety RN 71-4963C, Jun. 4, 2008.
Plant Variety Breeder's Certificate, for Carrot (*Daucus carota*) Variety NUTRI-RED, dated Apr. 28, 2006, France.
Plant Variety Breeder's Certificate, for Carrot (*Daucus carota*) Variety NUTRI-RED, dated Apr. 28, 2006, France. (English).
Plant Variety Breeder's Certificate No. 1780, for Carrot (*Daucus carota*) Variety NUTRI-RED, dated Nov. 25, 2003, Belgium.
Plant Variety Breeder's Certificate No. 1780, for Carrot (*Daucus carota*) Variety NUTRI-RED, dated Nov. 25, 2003, Belgium. (English).
Certificate of Plant Variety Protection Grant No. 03182, for Carrot (*Daucus carota*) Variety NUTRI-RED, dated Dec. 10, 2002, Austria.
Certificate of Plant Variety Protection Grant No. 03182, for Carrot (*Daucus carota*) Variety NUTRI-RED, dated Dec. 10, 2002, Austria. (English).
Plant Breeders' Certificate No. 7425 for Carrot (*Daucus carota*) Variety NUTRI-RED, dated Nov. 1, 2002, Great Britain.
Response to Office Action regarding U.S. Appl. No. 12/605,632 dated Dec. 29, 2011.
Chen et al., "Transgenic herbicide- and disease-tolerant carrot (*Daucus carota*L.) plants obtained through *Agrobacterium*-mediated transformation," *Plant Cell Rep*. 20:929-935, 2002.
U.S. Plant Variety Protection Certificate No. 9900093 for "BetaKing" carrot, Mar. 23, 2001.
Office Action regarding U.S. Appl. No. 12/605,632, dated Sep. 28, 2011.
Database WPI Week 200716, Thomson Scientific, London, GB: An 2007-155075, XP002473610, & JP 2007 014205 A (Takii Shubto KK) Jan. 25, 2007 Abstract.
English translation of Office Action issued Dec. 4, 2012, in Japanese Application No. 2009-533533.
Mayer-Biebach et al., "Thermal processing of carrots: Lycopene stability and isomerisation with regard to antioxidant potential", *Food Research International* 38:1103-1108, 2005.
Watanabe et al., "Carotenoid Pigments in Red, Orange and Yellow Root of Carrot (*Daucus carota* L.) Cultivars", *Nippon Shokuhin Kogyo Gakkaishi* 35(5):315-320, 1988 (English abstract).
Yamaguchi et al., "The Carotenoid Contents of the Kintoki and Kokubu Varieties of Carrots Grown in Japan", *Journal of the Japanese Society for Horticultural Science* 29(4):310-312, 1960.
USPTO: Notice of Allowance for U.S. Appl. No. 12/605,632, dated Mar. 19, 2012.
Simon et al., "Plant Pigments for Color and Nutrition," Hort. Science 32(1):12-13, 1997.
Simon et al., "Breeding Carrot, Cucumber, Onion and Garlic for Improved Quality and Nutritional Value," Hort. Bras. 11(2):171-173, 1993.
Buishand et al., "Investigations on the inheritance of color and carotenoid content in phloem and xylem of carrot roots (*Daucus carota*L.)," Euphytica 28(3):611-632, 1979.
Office Action issued Sep. 22, 2014, in Indian Application No. 2279/DELNP/2009.

\* cited by examiner

CARROTS HAVING INCREASED LYCOPENE CONTENT

This application claims the priority of U.S. provisional application Ser. No. 60/852,397, filed Oct. 18, 2006, and U.S. provisional application Ser. No. 60/905,809, filed Mar. 9, 2007, each of the disclosures of which are specifically incorporated herein by reference.

BACKGROUND OF THE INVENTION

A. Field of the Invention

The invention relates to the field of plant genetics and, more specifically, to the development of carrot plants having increased lycopene content.

B. Description of Related Art

Carrot (*Daucus carota* var *sativus*), a member of the Umbelliferae family, is one of the most important root crops and is grown on over 100,000 hectares worldwide. Carrots provide an excellent source of various vitamins and minerals, including vitamin A (beta-carotene), as well as dietary fiber content in animal diets. Breeding efforts over the last half century have resulted in a 75% increase in the beta-carotene content in cultivated carrots. Recently, interest in the nutritional value of other carrot pigments, such as xanthophylls, lycopene, anthocyanins, and other phytochemicals, has increased. Despite recent breeding efforts, there remains a need for the development of carrots having increased levels of carotenoids, other than beta-carotene, such as lycopene.

In general, the goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties often involves the development of homozygous inbred plants, the crossing of these plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

Carrots (*Daucus carota*) are one of the most important root crops and is grown on over 100,000 hectares worldwide. There are two main types of cultivated carrots. Eastern/Asiatic carrots are often called anthocyanin carrots because of their purple roots, although some have yellow roots. They typically have pubescent leaves giving them a gray-green color and bolt easily. They have slightly dissected leaves with branched roots and are an annual plant. Western or carotene carrots typically have orange, red or white roots. These carrots were most likely derived from the first group by selection among hybrid progenies of yellow Eastern carrots, white carrots and wild subspecies grown in the Mediterranean. The leaves are generally strongly dissected with unbranched roots and bright green, sparsely hairy foliage and are biennial.

The biennial carrot is a plant that only flowers every two years. In the first year the plant produces the edible root and a leafy top. If a carrot plant is left in the ground for another year, aided by a resting and cold vernalization period, it flowers and seeds are produced. Sexual reproduction in carrots can therefore be carried out as with other flowering plants.

The Western carrot is the most popular carrot and is subdivided into three groups: 1) short-rooted varieties that mature more quickly; such as Amsterdam Forcing, Tiana, Early French Frame, Early Nantes, Champion Scarlet Horn; 2) medium-rooted varieties, which are the most common type of commercially grown carrots and include varieties such as Mokum, Flakkee, Autumn King, Chantenay Red Cored, Royal Chantenay; and 3) long-rooted varieties, such as New Red Intermediate and Saint Valery.

Carrots are widely used as a fresh market or processed product. As a crop, carrots are grown commercially wherever environmental conditions permit the production of an economically viable yield. Carrots are highly regarded for their nutritional value and their storability. Carrots provide an excellent source of various vitamins and minerals, including vitamin A (beta-carotene), as well as dietary fiber content. Recently, interest in the nutritional value of other carrot pigments, such as xanthophylls, lycopene, anthocyanins, and other phytochemicals, has increased.

Historically, most carrot breeding methods involved mass selection and pedigree selection resulting in a great number of open-pollinated carrot varieties (Stein and Nothnagel, 1995). The first carrot hybrids were sold in the 1960s in the United States following the detection and analysis of male sterility in carrot by Thompson (1961) and Hanschke and Gabelman (1963). Hybrid breeding in carrot is generally based on two systems of cytoplasmic male sterility (CMS) with different genetic backgrounds and origin: "brown anther" type and "petaloid" type (Stein and Nothnagel, 1995). A third CMS system has been detected in an alloplasmic form originating from a cross between the wild carrot *D. carota gummifer* Hook. fil. and the cultivated carrot *D. c. sativus* Hoffm. (Nothnagel, 1992).

While breeding efforts to date have provided a number of useful carrot lines with beneficial traits, there remains a great need in the art for new lines with further improved traits. Such plants would benefit farmers and consumers alike by improving crop yields and/or quality.

SUMMARY OF THE INVENTION

The present invention relates to carrot lines having roots containing increased levels of lycopene, as well as containers of such carrots. The present invention also relates to parts of carrot plants from lines having roots with increased lycopene content, including seeds capable of growing carrot plants with increased root lycopene content.

The present invention also provides a seed of a carrot plant capable of producing a hybrid plant comprising roots having a lycopene content of at least 100 ppm, where a population of about 10 carrots contains an average lycopene content of between about 100 ppm and about 250 ppm.

The present invention also provides a method of producing a hybrid carrot seed comprising crossing a female parent having a lycopene content between about 100 ppm and about 200 ppm having cytoplasmic male sterility with a male carrot line having a lycopene content between about 100 ppm and about 200 ppm, and obtaining $F_1$ seed.

In still another aspect, the present invention is exemplified by plants or seeds of a carrot variety selected from red carrot hybrid 0710 0325, red carrot hybrid 0710 0339, red carrot hybrid 0710 0346, red carrot hybrid 710313, red carrot hybrid 710305, red carrot hybrid 710316, red carrot hybrid 710319, red carrot hybrid 710311, red carrot hybrid 710304, red carrot hybrid 710310, red carrot hybrid 710303, line RN 71-4963C, line RN 71-4904C, line RF 71-4911A, line RF 71-4912A, line RIF 71-4966C, line RIF 71-4967B, and line RIF 71-4968B. representative seeds of such varieties have been deposited with the ATCC as set forth herein below. As used herein, a plant of the invention includes any such plants.

In yet a further aspect, the present invention also provides hybrid carrot cultivar having a root comprising an increased lycopene level, where the lycopene content is measured as an average lycopene content of a plurality of roots obtained from the hybrid carrot cultivar compared to an average lycopene content of carrot roots obtained from Kintoki open pollinated variety carrots.

In another aspect, the present invention provides a carrot plant of the invention, as well as carrot plants having all the physiological and morphological characteristics of a plant of the invention. Parts of the carrot plant of the present invention are also provided, for example, including pollen, an ovule, a fruit, and a cell of the plant.

The carrot seed of the invention may be provided as an essentially homogeneous population of carrot seed of a plant of the invention. Essentially homogeneous populations of seed are generally free from substantial numbers of other seed. Therefore, seed may be defined as forming at least about 97% of the total seed, including at least about 98%, 99%, or more of the seed. The population of carrot seed may be particularly defined as being essentially free from hybrid seed. The seed population may be separately grown to provide an essentially homogeneous population of carrot plants of the invention.

In another aspect of the invention, a plant of the invention comprising an added heritable trait is provided. The heritable trait may comprise a genetic locus that is a dominant or recessive allele. In one embodiment of the invention, a plant of the invention is defined as comprising a single locus conversion. In specific embodiments of the invention, an added genetic locus confers one or more traits such as, for example, herbicide tolerance, insect resistance, disease resistance, and modified carbohydrate metabolism. The trait may be, for example, conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

In another aspect of the invention, a tissue culture of regenerable cells of a plant of the invention is provided. The tissue culture will preferably be capable of regenerating plants capable of expressing all of the physiological and morphological characteristics of the line, and of regenerating plants having substantially the same genotype as other plants of the line. Examples of such physiological and morphological characteristics include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides carrot plants regenerated from a tissue culture of the invention, the plants having all the physiological and morphological characteristics of a plant of the invention.

In yet another aspect of the invention, processes are provided for producing carrot seeds, plants and fruit, which processes generally comprise crossing a first parent carrot plant with a second parent carrot plant, wherein at least one of the first or second parent carrot plants is a plant of the invention. In one embodiment, the plant is selected from a line designated RN 71-4904C, RF 71-4911A, RF 71-4912A, RIF 71-4966C, RIF 71-4967B, or RIF 71-4968B. These processes may be further exemplified as processes for preparing hybrid carrot seed or plants, wherein a first carrot plant is crossed with a second carrot plant of a different, distinct line to provide a hybrid that has, as one of its parents, a carrot plant line provided herein. In these processes, crossing will result in the production of seed. The seed production occurs regardless of whether the seed is collected or not.

In one embodiment of the invention, the first step in "crossing" comprises planting seeds of a first and second parent carrot plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent carrot plants into plants that bear flowers. A third step may comprise preventing self-pollination of the plants, such as by emasculating the male portions of flowers, (i.e., treating or manipulating the flowers to produce an emasculated parent carrot plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent carrot plants. Yet another step comprises harvesting the seeds from at least one of the parent carrot plants. The harvested seed can be grown to produce a carrot plant or hybrid carrot plant.

The present invention also provides the carrot seeds and plants produced by a process that comprises crossing a first parent carrot plant with a second parent carrot plant, wherein at least one of the first or second parent carrot plants is a plant of the invention. In one embodiment of the invention, carrot seed and plants produced by the process are first generation ($F_1$) hybrid carrot seed and plants produced by crossing a plant in accordance with the invention with another, distinct plant. The present invention further contemplates plant parts of such an $F_1$ hybrid carrot plant, and methods of use thereof. Therefore, certain exemplary embodiments of the invention provide an $F_1$ hybrid carrot plant and seed thereof. For example, the invention provides plants and seeds of hybrid carrot variety 0710 0325, 0710 0339, or 0710 0346.

In still yet another aspect of the invention, the genetic complement of a carrot plant of the invention are provided. The phrase "genetic complement" is used to refer to the aggregate of nucleotide sequences, the expression of which sequences defines the phenotype of, in the present case, a carrot plant, or a cell or tissue of that plant. A genetic complement thus represents the genetic makeup of a cell, tissue or plant, and a hybrid genetic complement represents the genetic make up of a hybrid cell, tissue or plant. The invention thus provides carrot plant cells that have a genetic complement in accordance with the carrot plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that a plant of the invention could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by carrot plant cells, tissues, plants, and seeds, formed by the combination of a haploid genetic complement of a carrot plant of the invention with a haploid genetic complement of a second carrot plant, preferably, another, distinct carrot plant. In another aspect, the present invention provides a carrot plant regenerated from a tissue culture that comprises a hybrid genetic complement of this invention.

In still yet another aspect, the invention provides a plant of a carrot line, the roots of said plant exhibit a combination of traits comprising an average lycopene content from about 110 ppm to about 250 ppm and an average brix content from about 11° brix to about 20° brix, wherein the expression of the combination of traits is controlled by genetic means for the expression of the trait found in a carrot variety provided herein, including one or more of red carrot hybrid 0710 0325, red carrot hybrid 0710 0339, red carrot hybrid 0710 0346, red carrot hybrid 710313, red carrot hybrid 710305, red carrot hybrid 710316, red carrot hybrid 710319, red carrot hybrid 710311, red carrot hybrid 710304, red carrot hybrid 710310, red carrot hybrid 710303, line RN 71-4963C, line RN 71-4904C, line RF 71-4911A, line RF 71-4912A, line RIF 71-4966C, line RIF 71-4967B, and line RIF 71-4968B.

In still yet another aspect, the invention provides a method of determining the genotype of a plant of carrot line or variety disclosed herein comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from a line or variety disclosed herein the method comprising the steps of: (a) preparing a progeny plant derived from the line or variety, wherein said preparing comprises crossing a plant of a plant of the invention with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from the line or variety. The derived plant may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant is obtained which possesses some of the desirable traits of the line as well as potentially other selected traits.

In another aspect of the invention, a plant of a carrot line or variety comprising an added heritable trait is provided. The heritable trait may comprise a genetic locus that is a dominant or recessive allele. In one embodiment of the invention, a plant of the invention is defined as comprising a single locus conversion. In specific embodiments of the invention, an added genetic locus confers one or more traits such as, for example, herbicide tolerance, insect resistance, disease resistance, and modified carbohydrate metabolism. The trait may be, for example, conferred by a naturally occurring gene introduced into the genome of the hybrid by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

In another aspect of the invention, a tissue culture of regenerable cells of a plant disclosed herein is provided. The tissue culture will preferably be capable of regenerating plants capable of expressing all of the physiological and morphological characteristics of the hybrid, and of regenerating plants having substantially the same genotype as other plants of the hybrid. Examples of some of the physiological and morphological characteristics of the lines and varieties provided herein include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides carrot plants regenerated from a tissue culture of the invention, the plants having all the physiological and morphological characteristics of a plant provided herein.

In still yet another aspect, the invention provides a container of hybrid or non-hybrid carrot seeds where roots grown from greater than 50% of the seeds have an increased lycopene content, where a population of about 50 roots grown from the seeds contains an average lycopene content of between about 100 ppm and 250 ppm.

In another aspect, the present invention provides a container of hybrid carrots having at least a portion of the carrots with increased lycopene content, where the increased lycopene content is measured as an average lycopene content in a population of at least about 10 carrots of between about 100 ppm and about 250 ppm.

These and other features and advantages of this invention are described in, or are apparent from, the following detailed description of various exemplary embodiments of the devices and methods according to this invention.

DETAILED DESCRIPTION OF THE INVENTION

The invention provides carrot plants and in particular carrot cultivars or lines having increased lycopene content. Such carrots can be referred to as high lycopene carrot varieties. In a certain aspects, the carrot plants are hybrid carrot plants. Also disclosed herein are carrot cultivars or lines having increased lycopene content and cytoplasmic male sterility.

Methods of breeding high lycopene carrot lines are also provided. Also disclosed herein are $F_1$ hybrids of the high lycopene carrots.

As part of this invention, long, cylindrical shaped carrots containing the carotenoid lycopene have been developed to fit market needs, including the processing needs for the cut and peel market segment. Lycopene has received much attention with regard to its anti-oxidant capability in warding off cancer development, particularly in the digestive tract. In some embodiments, the carrots provided by this invention can be used to produce a solid red colored pack of cut and peel product or mixed into a blend of red, orange and yellow carrots. Oversize carrots also provided by this invention may be used for juice production.

Any carrot plant having a suitable lycopene content can be used in conjunction with the present invention. Carrots with suitable lycopene levels can be used in the methods of the present invention. In a preferred aspect, the source of an increased lycopene content is an elite plant. In an aspect, suitable lycopene carrots may be produced by breeding with the following lycopene sources: Nutri-red, red Indian descent carrots, and Kintoki open pollinated lines. In one aspect, a lycopene source carrot can be identified by determining the lycopene level in a carrot root, for example as described below. In an aspect, a lycopene source carrot plant may be crossed with any inbred carrot line having desired properties.

The invention also provides methods and compositions relating to plants, seeds and derivatives of carrot line RN 71-4904C (previously designated 71 0302), RF 71-4911A, RF 71-4912A, RIF 71-4966C, RIF 71-4967B, or RIF 71-4968B. These lines show uniformity and stability within the limits of environmental influence for the traits described hereinafter. Each of the carrot lines RN 71-4904C, RF 71-4911A, RF 71-4912A, RIF 71-4966C, RIF 71-4967B, and RIF 71-4968B provides sufficient seed yield. By crossing with a distinct second plant, uniform $F_1$ hybrid progeny can be obtained.

Of the hybrid carrot varieties developed by this invention, 0710 0325, 0710 0339, and 0710 0346, exhibit a more slender and longer root shape, which, for example, makes them well suited for use in the cut and peel market segment.

In contrast other carrot varieties also developed as part of this invention, for example, carrot hybrid varieties 710313, 710305, 710316, 710319, 710311, 710304, 710310, and 710303 are heavier and broader in diameter, which, for example, makes them more applicable to the juicing market segment.

A. Origin and Breeding History of Carrot Lines and Hybrid Varieties

1. Development of Open Pollinated Inbred Carrot Line RN 71-4904C (Previously Designated 71 0302)

High lycopene carrot line RN 71-4904C was obtained as outlined below. This carrot line is the result of a pedigree breeding system, initiated with a fertile×fertile cross between 'Lycopene 71B' (a Seminis inbred line) and '7262B' (a USDA carrot release containing anthocyanin and carotene). The 'Lycopene 71B' is an M4 high lycopene selection from the Seminis carrot release 'Nutri-red'.

The breeding process can be summarized as follows:

| | |
|---|---|
| Fall Year 1 | Planted parental lines in Brawley, CA ('Lycopene 71B' and '7262B') |
| Spring, Year 2 | Harvested parental roots and crossed in Fertile × Fertile fashion. |
| Fall Year 2 | Planted Fertile × Fertile seed in California |
| Spring Year 3 | Harvested vigorous $F_1$ roots from the F × F population and self pollinate |
| Fall Year 3 | Planted $F_2$ population seed in California |
| Spring Year 4 | Made $F_2$ selections, one being a red colored, cylindrical shaped root. Made a 3 root small mass for $F_2M$ population. |
| Fall, Year 4 | Planted $F_2M$ population seed in California |
| Spring Year 5 | Selected the same root form as the $F_2$. Again, increased to $F_2M_2$ via 3 root mass population. |
| Fall Year 5 | Planted $F_2M_2$ population seed in California. |
| Spring Year 6 | Grew out $F_2M_2$ population, but not harvested. No breeding action taken. |
| Fall Year 6 | Replanted $F_2M_2$ population seed in California. |
| Spring Year 7 | Selected for same criteria as the $F_2M$ population. Increase via 4 root mass to produce the $F_2M_3$ generation. |
| Fall Year 7 | Planted $F_2M_3$ population seed in California. |
| Spring Year 8 | Selected for same criteria as in the $F_2M_2$ population. Increase via 3 root mass to produce the $F_2M_4$ generation. |
| Fall Year 8 | Planted $F_2M_4$ population seed in California. |
| Spring Year 9 | Selected for same criteria as in $F_2M_3$ population. Increase via a 12 root mass for a larger seed increase. |
| Fall Year 9 | Planted $F_2M_5$ population seed in California. |
| Spring, Year 10 | The name PSR 71 0302 was applied (subsequently changed to RN 71-4904C) and the trial observed. |
| Fall Year 10 | Planted $F_2M_6$ population seed in California, as well as the new male sterile lines developed for hybridization (see breeding process Example 4, below). |
| Spring Year 11 | Harvested roots of male sterile lines and pollinators. Transplanted stecklings into hybrid cage isolations. |
| Fall Year 11 | Planted hybrid seed in California. |
| Spring Year 12 | Harvested and selected the best performing hybrid combinations. |

During the breeding program, a red cylindrical shaped carrot type emerged from the $F_2$ population and was selected. Small mass selection for the 'Nantes' root shape was repeated, and dark red color expressed through the core resulted in a very stable and uniform style root. One line was selected for having a high level of uniformity from one root to the next to obtain seed quantities for presentation, using a 12 root mass and designated Red Nantes, also designated RN 71-4904C. Very little variability within the line was observed, other than that expressed by environmental influence within any field condition.

2. Development of Open Pollinated Inbred Carrot Lines

Open pollinated carrot lines are also obtained from crosses using Indian red carrot lines as one of the parents. One source of genetic diversity is from the Indian germplasm, but these sources are basically tropical or annual type carrots. This can make them less suitable for use in temperate climates. These landrace lines also tend to have defects such as early, nearly annual bolting behavior, severe forking and irregular root shapes, prolific root hair growth, extreme variability in root type, shape, lycopene content, or any other phenotypic characteristic.

These Indian lines contain several advantages however, such as: 1) ability to accumulate moderate levels of lycopene and 2) extreme genetic diversity, including excellent eating quality. This eating quality can be the result of high juice content and low terpenoid levels.

Thus, to develop other high lycopene plant material, the following breeding strategy may be used:

a) Indian descent (red) crossed with Lycopene 71B (red) (see above).

b) Indian descent (red) crossed with cut and peel material (orange) (S-D813B, see U.S. Pat. No. 6,787,685).

c) Nutri-red (red) crossed with cut and peel material (orange) (S-D813B, see U.S. Pat. No. 6,787,685).

For example, the following scheme was used:

| | |
|---|---|
| Fall, Year 1 | Planted parental lines in Brawley, CA ('Lycopene 71B', Indian germplasm, and S-D813B). |
| Spring Year 2 | Harvested parental roots and cross in Fertile × Fertile fashion. |
| Fall, Year 2 | Planted Fertile × Fertile seed in California |
| Spring Year 3 | Harvested vigorous $F_1$ roots from the F × F population and sib-mate for the $F_1M$ populations (simulated $F_2$). |
| Fall, Year 3 | Planted $F_1M$ population seed in California |
| Spring Year 4 | Made $F_1M$ selections, selecting for cut and peel style or any full, interesting carrot shapes of normal behavior and expressing red color. Observations indicated vast differences from the original Indian material, which is severely early in bolting (almost annual in behavior), tends to have multiple branched (forked) roots and prolific root hair growth. |
| September Fall, Year 4 | Planted $F_1M_2$ population seed in California |
| Spring Year 5 | Selected the same root form as the $F_1M$; increased to $F_1M_3$ via 2 or 3 root mass populations. |
| Fall, Year 5 | Planted $F_1M_3$ population seed in California. |
| Spring Year 6 | Selected for same criteria as the $F_1M_2$ population. Increased via 2 or 3 root mass to produce the $F_1M_4$ generation. |
| September Fall, Year 6 | Planted $F_1M_4$ population seed in California. |
| Spring Year 7 | Evaluated lines for possible use as parents. Chose most promising lines for hybrid development and parental increase. |
| Fall, Year 7 | Planted new hybrids and parentals for advancement and seed increase. |

3. Development of Cytoplasmic Male-Sterile Carrot Lines

Carrot lines containing cytoplasmic male sterility having increased lycopene content can be produced, for example, using crosses between open-pollinated Nutri-red lines and an orange male sterile variety to introduce the cytoplasmic male sterility into the high lycopene background.

For example, below is a breeding process that has been used for the development of male sterile, high lycopene lines:

| | |
|---|---|
| Fall, Year 1 | Planted Nutri-red (red) and Orange male sterile seed in Imperial Valley. |
| Spring, Year 2 | Harvested roots of Nutri-red and orange male sterile lines for $F_1$ hybrids. |
| Fall, Year 2 | Planted hybrid seed in California. |
| Spring, Year 3 | Harvested hybrids of Nutri-red and Orange roots (all orange) in preparation of first backcross. |
| Fall, Year 3 | Planted $BC_1$ seed in California. |
| Spring, Year 4 | Selected red roots within the $BC_1$ population and prepared for backcrossing to Nutri-red. |
| Fall, Year 4 | Planted $BC_2$ seed in California |
| Spring, Year 5 | Most backcrosses appeared to be nearly stable, though some orange roots were observed. Red roots were again selected and prepared for backcrossing to Nutri-red. |
| Fall, Year 5 | Planted $BC_3$ seed in California. |
| Spring, Year 6 | Harvested roots, 100% of all backcross populations have complete expression of increased lycopene phenotype. Selected best lines for hybrid production and possible increase. |
| Fall, Year 6 | Planted new hybrids and backcrossed lines for advancement and seed increase. |

Following the above program, carrot lines having increased lycopene content were been obtained, which also exhibited cytoplasmic male sterility.

4. Development of Hybrid Carrot Varieties Having High Lycopene Content

Hybrid carrots have been developed by crossing the open pollinators of Example 2 and 3 (male parents) with the male-sterile lines of Example 4 (female parents), and collecting the hybrid $F_1$ seeds. Several hybrid varieties have been developed that contain increased levels of lycopene. These are identified as hybrid varieties 710303, 710304, 710310, 710313, 710311, 710319, 710316, and 710305. After harvesting roots from the hybrid varieties, it was observed that hybrid line 710319 segregates for orange and red, and as such did not result in a high lycopene carrot. These hybrids comprise an average lycopene content in their roots of at least 115 ppm, as determined by HPLC.

5. Development of Carrot Line RF 71-4911A

The development of carrot line RF 71-4911A can be summarized as follows:

| | |
|---|---|
| September Year 0 | Planted Nutri-red and Orange male sterile seed in Imperial Valley. |
| February Year 1 | Harvested roots of Nutri-red and orange male steriles for $F_1$ hybrids. Planted individual roots selected from Nutri-red and made crosses with the male steriles, establishing new sub-line populations of Nutri-red with their respective hybrids. |
| September Year 1 | Planted hybrid seed and new sub-lines in California. |
| February Year 2 | Harvested hybrids of Nutri-red sub-lines and Orange roots (all orange) in preparation of first backcross to the respective sub-lines. |
| September Year 2 | Planted $BC_1$ seed in California with the respective sub-lines. |
| February Year 3 | Selected red roots within the $BC_1$ population and prepared for backcrossing, again, to the Nutri-red sub-lines. |
| September Year 3 | Planted $BC_2$ seed in California with the respective sub-lines. |
| February Year 4 | Most backcrosses appeared to be nearly stable, though some orange roots caused concern about the possible genetic inheritance. Red roots were again selected and prepared for backcrossing to Nutri-red sub-lines. |
| September Year 4 | Planted $BC_3$ seed in California with the respective sub-lines. |
| February Year 5 | Harvested roots and found that 100% of all backcross populations had complete expression of lycopene. Selected best lines for hybrid production and possible increase, one set of lines being RF 71-4911A & B. |
| September Year 5/6 | Planted new hybrids and backcross lines for potential advancement and seed increase. |
| February Year 6/7 | Evaluated and selected best hybrid combinations, including 0710 0325 and 0710 0339. |

Line RF 71-4911A has been self-pollinated and planted for a number of generations to produce the homozygosity and phenotypic stability to make this line useful in commercial seed production. No variant traits have been observed or are expected for this line.

Carrot line RF 71-4911A, being substantially homozygous, can be reproduced by planting seeds of the line, growing the resulting carrot plant under self-pollinating or sib-pollinating conditions and harvesting the resulting seeds using techniques familiar to one of skill in the art.

6. Development of Carrot Line RF 71-4912A

The development of carrot line RF 71-4912A can be summarized as follows:

| | |
|---|---|
| September Year 0 | Planted Nutri-red and Orange male sterile seed in Imperial Valley. |
| February Year 1 | Harvested roots of Nutri-red and orange male steriles for $F_1$ hybrids. Planted individual roots selected from Nutri-red and made crosses with the male steriles, establishing new sub-line populations of Nutri-red with their respective hybrids. |
| September Year 1 | Planted hybrid seed and new sub-lines in California. |
| February Year 2 | Harvested hybrids of Nutri-red sub-lines and Orange roots (all orange) in preparation of first backcross to the respective sub-lines. |
| September Year 2 | Planted $BC_1$ seed in California with the respective sub-lines. |
| February Year 3 | Selected red roots within the $BC_1$ population and prepared for backcrossing, again, to the Nutri-red sub-lines. |
| September Year 3 | Planted BC2 seed in California with the respective sub-lines. |
| February Year 4 | Most backcrosses appeared to be nearly stable, though some orange roots caused concern about the possible genetic inheritance. Red roots were again selected and prepared for backcrossing to Nutri-red sub-lines. |
| September Year 4 | Planted $BC_3$ seed in California with the respective sub-lines. |
| February Year 5 | Harvested roots and found that 100% of all backcross populations had complete expression of lycopene. Selected best lines for hybrid production and possible increase, one set of lines being RF 71-4912A & B. |
| September Year 5/6 | Planted new hybrids and backcross lines for potential advancement and seed increase. |
| February Year 6/7 | Evaluated and selected best hybrid combinations, including 0710 0346. |

Line RF 71-4912A has been self-pollinated and planted for a number of generations to produce the homozygosity and phenotypic stability to make this line useful in commercial seed production. No variant traits have been observed or are expected for this line.

Carrot line RF 71-4912A, being substantially homozygous, can be reproduced by planting seeds of the line, growing the resulting carrot plant under self-pollinating or sib-pollinating conditions and harvesting the resulting seeds using techniques familiar to one of skill in the art.

7. Development of Carrot Line RIF 71-4966C

The development of carrot line RIF 71-4966C can be summarized as follows:

| | |
|---|---|
| September Year 1 | Planted parental lines of Nutri-red and S-D813B in Imperial Valley steckling bed. |
| February Year 2 | Selected best parental roots within populations of Nutri-red and S-D813B for fertile × fertile crossing pattern. |
| September Year 2 | Planted $F_1$ seed from fertile × fertile crossing system. |
| February Year 3 | Selected known hybrid roots within the population for advancement to the $F_1M$ population. |
| September Year 3 | Planted $F_1M$ seed from the $F_1$ selected roots in Imperial Valley, California. |
| February Year 4 | Selected $F_1M$ roots with slender, cylindrical shape that would fit the cut and peel processing market. Also tasted each individual root for direct eating quality evaluation. Planted in a sib-mating breeding system. |
| September Year 4 | Planted $F_1M2$ population seed in Imperial Valley, California. |
| February Year 5 | Evaluated $F_1M_2$ population roots and selected for cylindrical shape, good eating quality and qualities for cut and peel processing. |

| | |
|---|---|
| September Year 5 | Planted F₁M₃ population seed in Imperial Valley, California. |
| February Year 6 | Evaluated sub-selections and found one line, designated RIF 71-4966C with uniform root shape and consistency. The decision was to test in a hybrid combination scheme. |
| September Year 6 | Planted new hybrids made from pollinator RIF 71-4966C in Imperial Valley, California. |
| February Year 7 | Evaluated and selected best hybrid combinations, including 0710 0325. |

Line RIF 71-4966C has been self-pollinated and planted for a number of generations to produce the homozygosity and phenotypic stability to make this line useful in commercial seed production. No variant traits have been observed or are expected for this line.

Carrot line RIF 71-4966C, being substantially homozygous, can be reproduced by planting seeds of the line, growing the resulting carrot plant under self-pollinating or sib-pollinating conditions and harvesting the resulting seeds using techniques familiar to one of skill in the art.

8. Development of Carrot Line RIF 71-4967B

The development of carrot line RIF 71-4967B can be summarized as follows:

| | |
|---|---|
| September Year 2 | Planted parental lines of Nutri-red and S-D813B in Imperial Valley steckling bed. |
| February Year 3 | Selected best parental roots within populations of Nutri-red and S-D813B for fertile × fertile crossing pattern. |
| September Year 3 | Planted F₁ seed from fertile × fertile crossing system in Imperial Valley, California. |
| February Year 4 | Selected known hybrid roots within the population for advancement to the F₁M population. |
| September Year 4 | Planted F₁M seed from the F₁ selected roots in Imperial Valley, California. |
| February Year 5 | Selected F₁M roots with slender, cylindrical shape that would fit the cut and peel processing market. Also tasted each individual root for direct eating quality evaluation. Found one root with exceptional eating quality and shape and self pollinated. |
| September Year 5 | Planted F₁MS population seed in Imperial Valley, California. |
| February Year 6 | Evaluated the selfed line and designated it RIF 71-4967B with uniform root shape and consistency. The decision was to test in a hybrid combination scheme. |
| September Year 6 | Planted new hybrids made from pollinator RIF 71-4967B in Imperial Valley, California. |
| February Year 7 | Evaluated and selected best hybrid combinations, including 0710 0339. |

Line RIF 71-4967B has been self-pollinated and planted for a number of generations to produce the homozygosity and phenotypic stability to make this line useful in commercial seed production. No variant traits have been observed or are expected for this line.

Carrot line RIF 71-4967B, being substantially homozygous, can be reproduced by planting seeds of the line, growing the resulting carrot plant under self-pollinating or sib-pollinating conditions and harvesting the resulting seeds using techniques familiar to one of skill in the art.

9. Development of Carrot Line RIF 71-4968B

The development of carrot line RIF 71-4968B can be summarized as follows:

| | |
|---|---|
| September, Year 1 | Planted parental lines of Nutri-red and S-D813B in Imperial Valley steckling bed. |
| February, Year 2 | Selected best parental roots within populations of Nutri-red and S-D813B for fertile × fertile crossing pattern. |
| September, Year 2 | Planted F₁ seed from fertile × fertile crossing system. |
| February, Year 3 | Selected known hybrid roots within the population for advancement to the F₁M population. |
| September, Year 3 | Planted F₁M seed from the F₁ selected roots in Imperial Valley, California. |
| February, Year 4 | Selected F₁M roots with slender, cylindrical shape targeting the cut and peel processing market. Also tasted each individual root for direct eating quality evaluation. Planted in a sib-mating breeding system. |

| | |
|---|---|
| September Year 4 | Planted $F_1M_2$ population seed in Imperial Valley, California, |
| February Year 5 | Evaluated $F_1M_2$ population roots and selected for cylindrical shape, good eating quality and qualities for cut and peel processing. Found an individual root with exceptional eating quality and placed into a self pollinated scheme. |
| September Year 5 | Planted $F_1M_2S$ population seed in Imperial Valley, California. |
| February Year 6 | Evaluated the selfed line and designated it RIF 71-4968B with uniform root shape and consistency. The decision was to test in a hybrid combination scheme. |
| September Year 6 | Planted new hybrids made from pollinator RIF 71-4968B in Imperial Valley, California. |
| February Year 7 | Evaluated and selected best hybrid combinations, including 0710 0346. |

Line RIF 71-4968B has been self-pollinated and planted for a number of generations to produce the homozygosity and phenotypic stability to make this line useful in commercial seed production. No variant traits have been observed or are expected for this line.

Carrot line RIF 71-4968B, being substantially homozygous, can be reproduced by planting seeds of the line, growing the resulting carrot plant under self-pollinating or sib-pollinating conditions and harvesting the resulting seeds using techniques familiar to one of skill in the art.

10. Development of Hybrid Carrot Varieties Having High Lycopene Content

Hybrid carrots varieties 0710 0325, 0710 0339 and 0710 0346 resulted from the following crosses:

0710 0325=RF 71-4911A×RIF 71-4966C
0710 0339=RF 71-4911A×RIF 71-4967B
0710 0346=RF 71-4912A×RIF 71-4968B

B. Physiological and Morphological Characteristics of Carrot Varieties

The physiological and morphological characteristics of carrot hybrid and inbred varieties described herein are presented in Table 1-17. The values presented in the tables are typical values. Values may vary due to environment. Other values that are substantially equivalent are also within the scope of the invention.

TABLE 1

Physiological and Morphological Characteristics of Hybrid Variety PS 0710-0346

| CHARACTERISTIC | |
|---|---|
| 1. Type | Imperator |
|    Area of Best Adaptation in USA | Most Regions |
| 2. Maturity | |
|    Days from Seeding to Harvest | 110 |
| 3. Plant Top (Harvest Stage) | |
|    Habit | Semi-Erect |
|    Height from Shoulder to Top of Crown | 50 cm |
|    Neck Diameter | 35 mm |
|    Top Attachment | Single |
| 4. Leaf (Harvest Stage) | |
|    Blade Color | N134B in RHS Color Chart |
|    Blade Divisions | Medium |
|    Blade Length (W/O Petiole) | 25 cm |
|    Petiole Length from Crown to First Pinna | 20 cm |
|    Petiole Anthocyanin | Absent |
|    Petiole Pubescence | Absent |

TABLE 1-continued

Physiological and Morphological Characteristics of Hybrid Variety PS 0710-0346

| CHARACTERISTIC | |
|---|---|
| 5. Root | |
|    Cortex (Phloem) Thickness (Midpoint X-Section) | 11 mm |
|    Core (Xylem) Thickness (Midpoint X-Section) | 8 mm |
|    Carrot Length (Minus Taproot) | 30 cm |
|    Length of Taproot | 20 mm |
|    Diameter at Shoulder | 28 mm |
|    Diameter t Midpoint | 19 mm |
|    Amount Exposed (Above Ground) | None |
|    Shape | Conic |
|    Collar | Level |
|    Shoulder | Sloping |
|    Base | Medium |
|    Surface Smoothness | Very Smooth |
|    Number Secondary Root Scars | Few |
|    Appearance of Secondary Root Scars | Prominent |
|    Halo | Faint |
|    Zoning | Faint |
|    Flavor Harshness | Mild Harsh |
|    Flavor Sweetness | Moderate Sweet |
| 6. Colors | |
|    Above Ground Exterior Color, Shoulder | Red (60A in RHS Color Chart) |
|    Above Ground Exterior Color, Skin | Red (60A in RHS Color Chart) |
|    Below Ground Exterior Color, Shoulder | Red (60A in RHS Color Chart) |
|    Below Ground Exterior Color, Skin | Red (60A in RHS Color Chart) |
|    X-Section Interior Color, Xylem-(Core) | Red (60B in RHS Color Chart) |
|    X-Section Interior Color, Phloem | Red (60C in RHS Color Chart) |
| 7. Flower | |
|    Flower Color | 86 (193B in RHS Color Chart) |
|    Male Fertility | Male-Sterile |
|    Anthers | Petaloid |
| 8. Seeds | |
|    Height of Seed Stalk | 105 cm |
|    Stalk Pubescence | Little |
|    Diameter of First Order Umbel | 100 mm |
|    Seed Spines | Present |
|    per 100 Seeds | 200 mg |
| 9. Disease Reaction | |
|    Alternaria Blight | Susceptible |
|    Cavity Spot | Susceptible |
|    Powdery Mildew | Susceptible |
|    Pythium Root Dieback | Susceptible |

TABLE 1-continued

Physiological and Morphological Characteristics of Hybrid Variety PS 0710-0346

| CHARACTERISTIC | | |
|---|---|---|
| 10. Insect Reaction | | |
| Root Knot Nematode | Susceptible | |
| 11. Physiological Reaction | | |
| Bolting | Resistant | |
| Root Splitting | Resistant | |

TABLE 2

Physiological and Morphological Characteristics of Hybrid Variety PS 0710-0339

| CHARACTERISTIC | | |
|---|---|---|
| 1. Type | Imperator | |
| Area of Best Adaptation in USA | Most Regions | |
| 2. Maturity | | |
| Days from Seeding to Harvest | 110 | |
| 3. Plant Top (Harvest Stage) | | |
| Habit | Semi-Erect | |
| Height from Shoulder to Top of Crown | 45 cm | |
| Neck Diameter | 35 mm | |
| Top Attachment | Single | |
| 4. Leaf (Harvest Stage) | | |
| Blade Color | Dark Green, N132B in RHS Color Chart | |
| Blade Divisions | Medium | |
| Blade Length (W/O Petiole) | 28 cm | |
| Petiole Length from Crown to First Pinna | 20 cm | |
| Petiole Anthocyanin | Absent | |
| Petiole Pubescence | Absent | |
| 5. Root | | |
| Cortex (Phloem) Thickness (Midpoint X-Section) | 10 mm | |
| Core (Xylem) Thickness (Midpoint X-Section) | 7 mm | |
| Carrot Length (Minus Taproot) | 30 cm | |
| Length of Taproot | 20 mm | |
| Diameter at Shoulder | 24 mm | |
| Diameter t Midpoint | 17 mm | |
| Amount Exposed (Above Ground) | None | |
| Shape | Conic | |
| Collar | Level | |
| Shoulder | Sloping | |
| Base | Medium | |
| Surface Smoothness | Very Smooth | |
| Number Secondary Root Scars | Few | |
| Appearance of Secondary Root Scars | Not Prominent | |
| Halo | Faint | |
| Zoning | Faint | |
| Flavor Harshness | Moderate Harsh | |
| Flavor Sweetness | Moderate Sweet | |
| 6. Colors | | |
| Above Ground Exterior Color, Shoulder | Red (60B in RHS Color Chart) | |
| Above Ground Exterior Color, Skin | Red (60B in RHS Color Chart) | |
| Below Ground Exterior Color, Shoulder | Red (60B in RHS Color Chart) | |
| Below Ground Exterior Color, Skin | Red (60B in RHS Color Chart) | |
| X-Section Interior Color, Xylem-Core | Red (60C in RHS Color Chart) | |
| X-Section Interior Color, Phloem | Red (60D in RHS Color Chart) | |
| 7. Flower | | |
| Flower Color | 86 (193B in RHS Color Chart) | |
| Male Fertility | Male-Sterile | |
| Anthers | Petaloid | |
| 8. Seeds | | |
| Height of Seed Stalk | 100 cm | |
| Stalk Pubescence | Little | |
| Diameter of First Order Umbel | 110 mm | |
| Seed Spines | Present | |
| per 100 Seeds | 205 mg | |
| 9. Disease Reaction | | |
| Alternaria Blight | Susceptible | |
| Cavity Spot | Susceptible | |
| Powdery Mildew | Susceptible | |
| Pythium Root Dieback | Susceptible | |
| 10. Insect Reaction | | |
| Root Knot Nematode | Susceptible | |
| 11. Physiological Reaction | | |
| Bolting | Resistant | |
| Root Splitting | Resistant | |

TABLE 3

Physiological and Morphological Characteristics of Hybrid Variety PS 0710-0325

| CHARACTERISTIC | |
|---|---|
| 1. Type | Cut and Peel |
| Area of Best Adaptation in USA | Most Regions |
| 2. Maturity | |
| Days from Seeding to Harvest | 110 |
| 3. Plant Top (Harvest Stage) | |
| Habit | Semi-Erect |
| Height from Shoulder to Top of Crown | 45 cm |
| Neck Diameter | 30 mm |
| Top Attachment | Single |
| 4. Leaf (Harvest Stage) | |
| Name of Color Chart | RHS Color Chart |
| Blade Color | Dark Green, 135B in RHS Color Chart |
| Blade Divisions | Medium |
| Blade Length (W/O Petiole) | 25 cm |
| Petiole Length from Crown to First Pinna | 20 cm |
| Petiole Anthocyanin | Absent |
| Petiole Pubescence | Absent |

TABLE 3-continued

Physiological and Morphological Characteristics of Hybrid Variety PS 0710-0325

| CHARACTERISTIC | |
|---|---|
| 5. Root | |
| Cortex (Phloem) Thickness (Midpoint X-Section) | 8 mm |
| Core (Xylem) Thickness (Midpoint X-Section) | 7 mm |
| Carrot Length (Minus Taproot) | 28 cm |
| Length of Taproot | 20 mm |
| Diameter at Shoulder | 20 mm |
| Diameter at Midpoint | 15 mm |
| Amount Exposed (Above Ground) | None |
| Shape | Cylindrical |
| Collar | Level |
| Shoulder | Sloping |
| Base | Blunt |
| Surface Smoothness | Very Smooth |
| Number Secondary Root Scars | Few |
| Appearance of Secondary Root Scars | Not Prominent |
| Halo | None |
| Zoning | None |
| Flavor Harshness | Mild Harsh |
| Flavor Sweetness | Moderate Sweet |
| 6. Colors | |
| Above Ground Exterior Color, Shoulder | Red (60C in RHS Color Chart) |
| Above Ground Exterior Color, Skin | Red (60C in RHS Color Chart) |
| Below Ground Exterior Color, Shoulder | Red (60C in RHS Color Chart) |
| Below Ground Exterior Color, Skin | Red (60C in RHS Color Chart) |
| X-Section Interior Color, Xylem-Core | Red (61B in RHS Color Chart) |
| X-Section Interior Color, Phloem | Red (60D in RHS Color Chart) |
| 7. Flower | |
| Flower Color | 86 (193B in RHS Color Chart) |
| Male Fertility | Male-Sterile |
| Anthers | Petaloid |
| 8. Seeds | |
| Height of Seed Stalk | 105 cm |
| Stalk Pubescence | Little |
| Diameter of First Order Umbel | 110 mm |
| Seed Spines | Present |
| per 100 Seeds | 200 mg |
| 9. Disease Reaction | |
| *Alternaria* Blight | Susceptible |
| Cavity Spot | Susceptible |
| Powdery Mildew | Susceptible |
| *Pythium* Root Dieback | Susceptible |
| 10. Insect Reaction | |
| Root Knot Nematode | Susceptible |
| 11. Physiological Reaction | |
| Bolting | Resistant |
| Root Splitting | Resistant |

TABLE 4

Physiological and Morphological Characteristics of Variety RF 71-4912A and a Comparative Variety

| RF 71-4912A | Nutri-red |
|---|---|
| 1. TYPE: | |
| Imperator | Imperator |
| 2. Region Of Best Adaptation In U.S.A.: | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 44 cm | Plant Top Height: 50 cm |
| Neck Diameter: 140 mm | Top Diameter: 30 cm |
| Top Attachment: Single | Top Attachment: Single |

TABLE 4-continued

Physiological and Morphological Characteristics of Variety RF 71-4912A and a Comparative Variety

| RF 71-4912A | Nutri-red |
|---|---|
| 5. Leaf (At Harvest Stage) | |
| Name of Color Chart: RHS Colour Chart | Name of Color Chart: RHS Colour Chart |
| Blade Color: Dark Green | Leaf Blade Color: Dark Green |
| Color Chart Notation: 132B | Color Chart Notation: N134A |
| Blade Divisions: Medium | Leaf Blade Divisions: Medium |
| Blade Length (Without Petiole):; 26 cm | Leaf Blade Length: 30 cm |
| Petiole Length from Crown to First Pinna: 15 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 18 mm | Cortex Thickness: 10 mm |
| Core (Xylem) Thickness (Midpoint X-Section): 14 mm | Core Thickness: 10 mm |
| Carrot Length (Minus Taproot): 27 cm | Carrot Length (Minus Taproot): 24 cm |
| Length of Taproot: 20 mm | Length of Taproot: 20 mm |
| Diameter at Shoulder: 38 mm | Diameter at Shoulder: 32 mm |
| Diameter at Midpoint: 33 mm | Diameter at Midpoint: 22 mm |
| Amount Exposed (Above Ground): None | Amount Exposed(Above Ground): None |
| Shape: Conic | Root Shape: Conic |
| Collar: Level | Collar: Level |
| Shoulder: Sloping | Shoulder: Sloping |
| Base: Medium | Base: Pointed |
| Surface Smoothness: Dimpled or Corrugated | Surface Smoothness: Dimpled or Corrugated |
| Number Secondary Root Scars: Few | Number Secondary Root Scars: Few |
| Appearance of Secondary Root Scars: Prominent | Appearance of Secondary Root Scars: Prominent |
| Halo: Faint | Halo: Faint |
| Zoning: Faint | Zoning: Faint |
| Flavor Harshness: Moderate Harsh | Flavor Harshness: Very harsh |
| Flavor Sweetness: Moderate Sweet | Flavor Sweetness: Not sweet |
| 7. Flower | |
| Flower Color: 06 (Color Chart Notation 194B) | Flower Color: 01 (Color Chart Notation N155D) |
| Male Fertility: Male-Sterile | Fertility: Fertile |
| Anthers: Petaloid | Anthers: Normal |
| 8. Seed | |
| Height of Seed Stalk: 120 cm | Height of Seed Stalk: 95 cm |
| Stalk Pubescence: Little | Stalk Pubescence: Little |
| Diameter of First Order Umbel: 130 mm | Diameter of First Order Umbel: 120 mm |
| Seed Spines: Present | Seed Spines: Present |
| 230 mg per 100 Seeds | 210 mg per 100 Seeds |
| 9. Disease Reaction | |
| *Alternaria* Blight: Susceptible | *Alternaria* Blight: Susceptible |
| *Aster* Yellows: Susceptible | *Aster* Yellows: Susceptible |
| *Sclerotinia* Decay: Susceptible | Cavity Spot: Susceptible |
| | Motley Dwarf Virus: Susceptible |
| | Powdery Mildew: Susceptible |
| | *Pythium* Root Dieback: Susceptible |
| | *Sclerotinia* Decay: Susceptible |
| 10. Insect Reaction | |
| Root Knot Nematode: Susceptible | Root Knot Nematode: Susceptible |
| 11. Physiological Reaction | |
| Bolting: Resistant | Bolting: Resistant |
| Root Splitting: Resistant | Root Splitting: Resistant |

TABLE 5

Physiological and Morphological Characteristics of Variety 0710 0319 and a Comparative Variety

| 0710 0319 | Nutri-red |
|---|---|
| 1. Type | |
| Imperator | Imperator |
| 2. Region Of Rest Adaptation In U.S.A | |
| Most Regions | Most Regions |
| 3. Market Maturity | |
| No. Days from Seeding to Harvest: 110 | No. Days to Market Maturity: 120 |
| 4. Plant Top (At Harvest Stage) | |
| Habit: Semi-erect | Habit: Semi-erect |
| Height from Shoulder to Top of Crown: 1.0 cm | Plant Top Height: 50 cm |
| Neck Diameter: 18 mm | Top Diameter: 300 mm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Coarse | Leaf Blade Divisions: Medium |
| Blade Length (Without Petiole): 30 cm | Leaf Blade Length: 30 cm |
| Petiole Length from Crown to First Pinna: 25 cm | Leaf Petiole Length: 20 cm |
| Petiole Anthocyanin: Present | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 12 mm | Cortex Thickness: 10 mm |
| Core (Xylem) Thickness (Midpoint X-Section): 13 mm | Core Thickness: 10 mm |
| Carrot Length (Minus Taproot): 26 cm | Carrot Length: 24 cm |
| Length of Taproot: 20 mm | Length of Taproot: 20 mm |
| Diameter at Shoulder: 38 mm | Diameter at Shoulder: 32 mm |
| Diameter at Midpoint: 28 mm | Diameter at Midpoint: 22 mm |
| Amount Exposed (Above Ground): 1-10% | Amount Exposed: None |
| Shape: Conic | Root Shape: Conic |
| Collar: Level | Collar: Level |
| Shoulder: Sloping | Shoulder: Sloping |
| Base: Medium | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Prominent | Appearance of Secondary Roots: Prominent |
| Halo: Prominent | Halo: Faint |
| Zoning: Prominent | Zoning: Faint |
| Flavor Harshness: Mildly Harsh | Flavor Harshness: Very harsh |
| Flavor Sweetness: Moderately Sweet | Flavor Sweetness: Not sweet |
| | Name of Color Chart: RHS Colour |
| Colors: | |
| Above Ground Exterior Color: 94 Shoulder (Color Chart Notation 60B) | 84 Shoulder (Color Chart Notation 59D) |
| Above Ground Exterior Color: 94 Skin (Color Chart Notation 60B) | Skin: 84 (Color Chart Notation 59D) |
| Below Ground Exterior Color: 94 Shoulder (Color Chart Notation 60B) | Shoulder: 84 (Color Chart Notation 59D) |
| Below Ground Exterior Color: 94 Skin (Color Chart Notation 60B) | Skin: 84 (Color Chart Notation 59D) |
| X-Section Interior Color: 04 Xylem (Core) (Color Chart Notation 60C) | Xylem: 84 (Color Chart Notation 63B) |
| X-Section Interior Color: 04 Phloem (Color Chart Notation 60C) | Phloem: 84 (Color Chart Notation 63A) |
| 7. Flower | |
| Flower Color: 86 (Color Chart Notation 193B) | Flower Color: 01 (Color Chart Notation N155D) |
| Male Fertility: Male-Sterile | Fertility: Fertile |
| Anthers: Petaloid | Anthers: Normal |
| 8. Seed | |
| Height of Seed Stalk: 95 cm | Height of Seed Stalk: 95 cm |
| Stalk Pubescence: Little | Stalk Pubescence: Little |
| Diameter of First Order Umbel: 105 mm | Diameter of First Order Umbel: 120 mm |
| Seed Spines: Present | Seed Spines: Present |
| 220 mg per 100 Seeds | 210 mg per 100 Seeds |
| 9. Disease Reaction (1 = Susceptible; 2 = Resistant; Give Races If Known) | |
| Alternaria Blight: Susceptible | Alternaria Blight: Susceptible |
| Aster Yellows: Susceptible | Aster Yellows: Susceptible |
| Cavity Spot: Susceptible | Cavity Spot: Susceptible |
| Cercospora Blight: Susceptible | |
| Motley Dwarf Virus: Susceptible | Motley Dwarf Virus: Susceptible |
| Powdery Mildew: Susceptible | Powdery Mildew: Susceptible |
| Pythium Root Dieback: Susceptible | Pythium Root Dieback: Susceptible |
| Sclerotinia Decay: Susceptible | Sclerotinia Decay: Susceptible |
| 10. Insect Reaction (1 = Susceptible; 2 = Resistant; give rates if known) | |
| Root Knot Nematode: Susceptible | Root Knot Nematode: Susceptible |
| 11. Physiological Reaction (1 = Susceptible; 2 = Resistant) | |
| Bolting: Susceptible | Bolting: Resistant |
| Root Splitting: Resistant | Root Splitting: Resistant |

Notes:
Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green, 7 = Salmon, 8 = Light, 9 = Dark
Color example: 0 2 = Yellow; 3 4 = Orange-Red; 9 4 Dark Red.

TABLE 6

Physiological and Morphological Characteristics of Variety 0710 0305 and a Comparative Variety

| 0710 0305 | Nutri-red |
|---|---|
| 1. Type: | |
| Nates | Imperator |
| 2. Region Of Best Adaptation In U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 12 mm | Top Diameter: 300 mm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 24 cm | Leaf Blade Length: 30 cm |
| Petiole Length from Crown to First Pinna: 20 cm | Leaf Petiole Length: 20 cm |
| Petiole Anthocyanin: Absent | Petiole Anthocyanin: Absent |
| Petiole Pubescence: Absent | Petiole Pubescence: Absent |

TABLE 6-continued

Physiological and Morphological Characteristics of Variety 0710 0305 and a Comparative Variety

| 0710 0305 | Nutri-red |
|---|---|
| 6. Root (At Market Maturity) | |
| Cortex (Phloem) Thickness (Midpoint X-Section): 9 mm | Cortex Thickness: 10 mm |
| Core (Xylem) Thickness (Midpoint X-Section): 8 mm | Core Thickness: 10 mm |
| Carrot Length (Minus Taproot): 16 cm | Carrot Length: 24 cm |
| Length of Taproot: 18 mm | Length of Taproot: 20 mm |
| Diameter at Shoulder: 26 mm | Diameter at Shoulder: 32 mm |
| Diameter at Midpoint: 21 mm | Diameter at Midpoint: 22 mm |
| Amount Exposed (Above Ground): 1-10% | Amount Exposed: None |
| Shape: Cylindrical | Root Shape: Conic |
| Collar: Level | Collar: Level |
| Shoulder: Rounded | Shoulder: Sloping |
| Base: Blunt | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mildly Harsh | Flavor Harshness: Very harsh |
| Flavor Sweetness: Very Sweet | Flavor Sweetness: Not sweet |
| Colors: | Name of Color Chart: RH |
| Above Ground Exterior Color: 94 Shoulder (Color Chart Notation 59B) | 84 Shoulder (Color Chart Notation 59D) |
| Above Ground Exterior Color: 94 Skin (Color Chart Notation 59B) | Skin: 84 (Color Chart Notation 59D) |
| Below Ground Exterior Color: 94 Shoulder (Color Chart Notation 59B) | Shoulder: 84 (Color Chart Notation 59D) |
| Below Ground Exterior Color: 94 Skin (Color Chart Notation 59B) | Skin: 84 (Color Chart Notation 59D) |
| X-Section Interior Color: 04 Xylem (Core) (Color Chart Notation 59C) | Xylem: 84 (Color Chart Notation 63B) |
| X-Section Interior Color: 04 Phloem (Color Chart Notation 59C) | Phloem: 84 (Color Chart Notation 63A) |
| 7. Flower | |
| Flower Color: 86 (Color Chart Notation 193B) | Flower Color: 01 (Color Chart Notation N115D) |
| Male Fertility: Male-Sterile | Fertility: Fertile |
| Anthers: Petaloid | Anthers: Normal |
| 8. Seed | |
| Height of Seed Stalk: 100 cm | Height of Seed Stalk: 95 cm |
| Stalk Pubescence: Little | Stalk Pubescence: Little |
| Diameter of First Order Umbel: 112 mm | Diameter of First Order Umbel: 120 mm |
| Seed Spines: Present | Seed Spines: Present |
| 205 mg per 100 Seeds | 210 mg per 100 Seeds |
| 9. Disease Reaction (1 = Suseeptible; 2 = Resistant; give rates if known) | |
| Alternaria Blight: Susceptible | Alternaria Blight: Susceptible |
| Aster Yellows: Susceptible | Aster Yellows: Susceptible |
| Cavity Spot: Susceptible | Cavity Spot: Susceptible |
| Cercospora Blight: Susceptible | |
| Motley Dwarf Virus: Susceptible | Motley Dwarf Virus: Susceptible |
| Powdery Mildew: Susceptible | Powdery Mildew: Susceptible |
| Pythium Root Dieback: Susceptible | Pythium Root Dieback: Susceptible |
| Sclerotinia Decay: Susceptible | Sclerotinia Decay: Susceptible |
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

Notes:
Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green, 7 = Salmon, 8 = Light, 9 = Dark
Color examples: 0 2 = Yellow; 3 4 = Orange-Red; 9 4 Dark Red.

TABLE 7

Physiological and Morphological Characteristics of Variety 0710 0304 and a Comparative Variety

| 0710 0304 | Nutri-red |
|---|---|
| 1. Type | |
| Nantes | Imperator |
| 2. Region of Best Adaptation in U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 11 mm | Top Diameter: 300 mm |
| Top Attachment: Single | Top Attachment: Single |
| 5. Lear (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 26 cm | Leaf Blade Length: 30 cm |
| Petiole Length from Crown to First Pinna: 22 cm | Leaf Petiole Length: 20 cm |
| Petiole Anthocyanin: Absent | Petiole Anthocyanin: Absent |
| Petiole Pubescence: Absent | Petiole Pubescence: Absent |

TABLE 7-continued

| | |
|---|---|
| 6. Root (At Market Maturity) | |
| Cortex (Phloem) Thickness (Midpoint X-Section): 11 mm | Cortex Thickness: 10 mm |
| Core (Xylem) Thickness (Midpoint X-Section): 9 mm | Core Thickness: 10 mm |
| Carrot Length (Minus Taproot): 18 cm | Carrot Length: 24 cm |
| Length of Taproot: 18 mm | Length of Taproot: 20 mm |
| Diameter at Shoulder: 24 mm | Diameter at Shoulder: 32 mm |
| Diameter at Midpoint: 19 mm | Diameter at Midpoint: 22 mm |
| Amount Exposed (Above Ground): 1-10% | Amount Exposed: None |
| Shape: Cylindrical | Root Shape: Conic |
| Collar: Level | Collar: Level |
| Shoulder: Rounded | Shoulder: Sloping |
| Base: Blunt | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mildly Harsh | Flavor Harshness: Very harsh |
| Flavor Sweetness: Very Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green,
7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 59B) | 84 Shoulder (Color Chart Notation 59D) |
| Above Ground Exterior Color: 94 Skin (Color Chart Notation 59B) | Skin: 84 (Color Chart Notation 59D) |
| Below Ground Exterior Color: 94 Shoulder (Color Chart Notation 59B) | Shoulder: 84 (Color Chart Notation 59D) |
| Below Ground Exterior Color: 94 Skin (Color Chart Notation 59B) | Skin: 84 (Color Chart Notation 59D) |
| X-Section Interior Color: 04 Xylem (Core) (Color Chart Notation 59C) | Xylem: 84 (Color Chart Notation 63B) |
| X-Section Interior Color: 04 Phloem (Color Chart Notation 59C) | Phloem: 84 (Color Chart Notation 63A) |
| 7. Flower | |
| Flower Color: 86 (Color Chart Notation 193B) | Flower Color: 01 (Color Chart Notation N155D) |
| Male Fertility: Male-Sterile | Fertility: Fertile |
| Anthers: Petaloid | Anthers: Normal |
| 8. Seed | |
| Height of Seed Stalk: 95 cm | Height of Seed Stalk: 95 cm |
| Stalk Pubescence: Little | Stalk Pubescence: Little |
| Diameter of First Order Umbel: 110 mm | Diameter of First Order Umbel: 120 mm |
| Seed Spines: Present | Seed Spines: Present |
| 220 mg per 100 Seeds | 210 mg per 100 Seeds |
| 9. Disease Reaction (1 = Susceptible; 2 = Resistant; give races if known) | |
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

TABLE 8

Physiological and Morphological Characteristics of Variety 0710 0310 and a Comparative Variety

| 0710 0310 | Nutri-red |
|---|---|
| 1. Type | |
| Nantes | Imperator |
| 2. Region of Best Adaptation in U.S.A | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 13 mm | Top Diameter: 300 mm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 28 cm | Leaf Blade Length: 30 cm |
| Petiole Length from Crown to First Pinna: 21 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 10 mm | Cortex Thickness: 10 mm |
| Core (Xylem) Thickness (Midpoint X-Section): 8 mm | Core Thickness: 10 mm |
| Carrot Length (Minus Taproot): 16 cm | Carrot Length: 24 cm |
| Length of Taproot: 18 mm | Length of Taproot: 20 mm |
| Diameter at Shoulder: 22 mm | Diameter at Shoulder: 32 mm |
| Diameter at Midpoint: 16 mm | Diameter at Midpoint: 22 mm |
| Amount Exposed (Above Ground): 1-10% | Amount Exposed: None |
| Shape: Cylindrical | Root Shape: Conic |
| Collar: Level | Collar: Level |
| Shoulder: Rounded | Shoulder: Sloping |
| Base: Blunt | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mildly Harsh | Flavor Harshness: Very harsh |
| Flavor Sweetness: Very Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green, 7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 59B) | 84 Shoulder (Color Chart Notation 59D) |
| Above Ground Exterior Color: 94 Skin (Color Chart Notation 59B) | Skin: 84 (Color Chart Notation 59D) |
| Below Ground Exterior Color: 94 Shoulder (Color Chart Notation 59B) | Shoulder: 84 (Color Chart Notation 59D) |
| Below Ground Exterior Color: 94 Skin (Color Chart Notation 59B) | Skin: 84 (Color Chart Notation 59D) |
| X-Section Interior Color: 04 Xylem (Core) (Color Chart Notation 59C) | Xylem: 84 (Color Chart Notation 63B) |
| X-Section Interior Color: 04 Phloem (Color Chart Notation 59C) | Phloem: 84 (Color Chart Notation 63A) |
| 7. Flower | |
| Flower Color: 86 (Color Chart Notation 193B) | Flower Color: 01 (Color Chart Notation N155D) |
| Male Fertility: Male-Sterile | Fertility: Fertile |
| Anthers: Petaloid | Anthers: Normal |

TABLE 8-continued

8. Seed
   Height of Seed Stalk: 90 cm — Height of Seed Stalk: 95 cm
   Stalk Pubescence: Little — Stalk Pubescence: Little
   Diameter of First Order Umbel: 115 mm — Diameter of First Order Umbel: 120 mm
   Seed Spines: Present — Seed Spines: Present
   210 mg per 100 Seeds — 210 mg per 100 Seeds
9. Disease Reaction (1 = Susceptible; 2 = Resistant; give races if known)
   *Alternaria* Blight: Susceptible — *Alternaria* Blight: Susceptible
   *Aster* Yellows: Susceptible — *Aster* Yellows: Susceptible
   Cavity Spot: Susceptible — Cavity Spot: Susceptible
   *Cercospora* Blight: Susceptible
   Motley Dwarf Virus: Susceptible — Motley Dwarf Virus: Susceptible
   Powdery Mildew: Susceptible — Powdery Mildew: Susceptible
   *Pythium* Root Dieback: Susceptible — *Pythium* Root Dieback: Susceptible
   *Sclerotinia* Decay: Susceptible — *Sclerotinia* Decay: Susceptible
10. Insect Reaction (1 = Susceptible; 2 = Resistant; give races if known)
    Root Knot Nematode: Susceptible — Root Knot Nematode: Susceptible
11. Physiological Reaction (1 = Susceptible; 2 = Resistant)
    Bolting: Resistant — Bolting: Resistant
    Root Splitting: Resistant — Root Splitting: Resistant

TABLE 9

Physiological and Morphological Characteristics of Variety 0710 0311 and a Comparative Variety

| 0710 0311 | Nutri-red |
|---|---|
| 1. Type | |
| Nantes | Imperator |
| 2. Region of Best Adaptation In U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 10 mm | Top Diameter: 300 mm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 28 cm | Leaf Blade Length: 30 cm |
| Petiole Length from Crown to First Pinna: 22 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 10 mm | Cortex Thickness: 10 mm |
| Core (Xylem) Thickness (Midpoint X-Section): 8 mm | Core Thickness: 10 mm |
| Carrot Length (Minus Taproot): 17 cm | Carrot Length: 24 cm |
| Length of Taproot: 18 mm | Length of Taproot: 20 mm |
| Diameter at Shoulder: 22 mm | Diameter at Shoulder: 32 mm |
| Diameter at Midpoint: 20 mm | Diameter at Midpoint: 22 mm |
| Amount Exposed (Above Ground): 1-10% | Amount Exposed: None |
| Shape: Cylindrical | Root Shape: Conic |
| Collar: Level | Collar: Level |
| Shoulder: Rounded | Shoulder: Sloping |
| Base: Blunt | Base: Pointed |
| Surface Smoothness: Dimpled or Corrugated | Surface Smoothness: Dimpled or Corrugated |

TABLE 9-continued

| | |
|---|---|
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mildly Harsh | Flavor Harshness: Very harsh |
| Flavor Sweetness: Very Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green,
7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 59B) | 84 Shoulder (Color Chart Notation 59D) |
| Above Ground Exterior Color: 94 Skin (Color Chart Notation 59B) | Skin: 84 (Color Chart Notation 59D) |
| Below Ground Exterior Color: 94 Shoulder (Color Chart Notation 59B) | Shoulder: 84 (Color Chart Notation 59D) |
| Below Ground Exterior Color: 94 Skin (Color Chart Notation 59B) | Skin: 84 (Color Chart Notation 59D) |
| X-Section Interior Color: 04 Xylem (Core) (Color Chart Notation 59C) | Xylem: 84 (Color Chart Notation 63B) |
| X-Section Interior Color: 04 Phloem (Color Chart Notation 59C) | Phloem: 84 (Color Chart Notation 63A) |

7. Flower

| | |
|---|---|
| Flower Color: 86 (Color Chart Notation 193B) | Flower Color: 01 (Color Chart Notation N155D) |
| Male Fertility: Male-Sterile | Fertility: Fertile |
| Anthers: Petaloid | Anthers: Normal |

8. Seed

| | |
|---|---|
| Height of Seed Stalk: 95 cm | Height of Seed Stalk: 95 cm |
| Stalk Pubescence: Little | Stalk Pubescence: Little |
| Diameter of First Order Umbel: 105 mm | Diameter of First Order Umbel: 120 mm |
| Seed Spines: Present | Seed Spines: Present |
| 210 mg per 100 Seeds | 210 mg per 100 Seeds |

9. Disease Reaction (1 = Susceptible; 2 = Resistant; give races if known)

| | |
|---|---|
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |

10. Insect Reaction (1 = Susceptible; 2 = Resistant; give races if known)

| | |
|---|---|
| Root Knot Nematode: Susceptible | Root Knot Nematode: Susceptible |

11. Physiological Reaction (1 = Susceptible; 2 = Resistant);

| | |
|---|---|
| Bolting: Resistant | Bolting: Resistant |
| Root Splitting: Resistant | Root Splitting: Resistant |

TABLE 10

Physiological and Morphological Characteristics of Variety 0710 0313 and a Comparative Variety

| 0710 0313 | Nutri-red |
|---|---|

1. Type

| | |
|---|---|
| Nantes | Red Imperator |

2. Region of Best Adaptation In U.S.A.

| | |
|---|---|
| Most Regions | Most Regions |

3. Market Maturity

| | |
|---|---|
| No. Days from Seeding to Harvest: 120 | No. Days to Market Maturity: 120 |

4. Plant Top (At Harvest Stage)

| | |
|---|---|
| Habit: Semi-erect | Habit: Semi-erect |
| Height from Shoulder to Top of Crown: 0.5 cm | Plant Top Height: 50 cm |
| Neck Diameter: 13 mm | Top Diameter: 30 cm |
| Top Attachment: Single | Top Attachment: Single |

TABLE 10-continued

| | |
|---|---|
| 5. Lear (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 26 cm | Leaf Blade Length: 30 cm |
| Petiole Length from Crown to First Pinna: 22 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 10 mm | Cortex Thickness: 10 mm |
| Core (Xylem) Thickness (Midpoint X-Section): 8 mm | Core Thickness: 10 mm |
| Carrot Length (Minus Taproot): 18 cm | Carrot Length: 24 cm |
| Length of Taproot: 18 mm | Length of Taproot: 20 mm |
| Diameter at Shoulder: 28 mm | Diameter at Shoulder: 32 mm |
| Diameter at Midpoint: 23 mm | Diameter at Midpoint: 22 mm |
| Amount Exposed (Above Ground): 1-10% | Amount Exposed: None |
| Shape: Cylindrical | Root Shape: Conic |
| Collar: Level | Collar: Level |
| Shoulder: Rounded | Shoulder: Sloping |
| Base: Blunt | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Moderate Harsh | Flavor Harshness: Very harsh |
| Flavor Sweetness: Moderate Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green, 7 = Salmon, 8 = Light, 9 = Dark
Color examples: 0 2 = Yellow; 3 4 = Orange-Red; 9 4 = Dark Red.

| | |
|---|---|
| Colors: | Name of Color Chart: RHS Colour |
| Above Ground Exterior Color: 94 Shoulder (Color Chart Notation 59B) | 84 Shoulder (Color Chart Notation 59D) |
| Above Ground Exterior Color: 94 Skin (Color Chart Notation 59B) | Skin: 84 (Color Chart Notation 59D) |
| Below Ground Exterior Color: 94 Shoulder (Color Chart Notation 59B) | Shoulder: 84 (Color Chart Notation 59D) |
| Below Ground Exterior Color: 94 Skin (Color Chart Notation 59B) | Skin: 84 (Color Chart Notation 59D) |
| X-Section Interior Color: 04 Xylem (Core) (Color Chart Notation 59C) | Xylem: 84 (Color Chart Notation 63B) |
| X-Section Interior Color: 04 Phloem (Color Chart Notation 59C) | Phloem: 84 (Color Chart Notation 63A) |
| 7. Flower | |
| Flower Color: 86 (Color Chart Notation 193B) | Flower Color: 01 (Color Chart Notation N155D) |
| Male Fertility: Male-Sterile | Fertility: Fertile |
| Anthers: Petaloid | Anthers: Normal |
| 8. Seed | |
| Height of Seed Stalk: 125 cm | Height of Seed Stalk: 95 cm |
| Stalk Pubescence: Little | Stalk Pubescence: Little |
| Diameter of First Order Umbel: 125 mm | Diameter of First Order Umbel: 120 mm |
| Seed Spines: Present | Seed Spines: Present |
| 210 mg per 100 Seeds | 210 mg per 100 Seeds |
| 9. Disease Reaction (1 = Susceptible; 2 = Resistant; give races if known) | |
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give rates if known) | |
| Root Knot Nematode: Susceptible | Root Knot Nematode: Susceptible |

TABLE 10-continued

11. Physiological Reaction (1 = Susceptible; 2 = Resistant)
    Bolting: Resistant                    Bolting: Resistant
    Root Splitting: Resistant             Root Splitting: Resistant

TABLE 11

Physiological and Morphological Characteristics of Variety 0710 0316 and a Comparative Variety

| 0710 0316 | Nutri-red |
|---|---|
| 1. Type | |
| Nantes | Imperator |
| 2. Region of Best Adaptation in U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 14 mm | Top Diameter: 300 mm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 26 cm | Leaf Blade Length: 30 cm |
| Petiole Length from Crown to First Pinna: 22 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 10 mm | Cortex Thickness: 10 mm |
| Core (Xylem) Thickness (Midpoint X-Section): 7 mm | Core Thickness: 10 mm |
| Carrot Length (Minus Taproot): 16 cm | Carrot Length: 24 cm |
| Length of Taproot: 18 mm | Length of Taproot: 20 mm |
| Diameter at Shoulder: 27 mm | Diameter at Shoulder: 32 mm |
| Diameter at Midpoint: 20 mm | Diameter at Midpoint: 22 mm |
| Amount Exposed (Above Ground): 1-10% | Amount Exposed: None |
| Shape: Cylindrical | Root Shape: Conic |
| Collar: Level | Collar: Level |
| Shoulder: Rounded | Shoulder: Sloping |
| Base: Blunt | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mildly Harsh | Flavor Harshness: Very harsh |
| Flavor Sweetness: Very Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green, 7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 59B) | 84 Shoulder (Color Chart Notation 59D) |
| Above Ground Exterior Color: 94 Skin (Color Chart Notation 59B) | Skin: 84 (Color Chart Notation 59D) |
| Below Ground Exterior Color: 94 Shoulder (Color Chart Notation 59B) | Shoulder: 84 (Color Chart Notation 59D) |
| Below Ground Exterior Color: 94 Skin (Color Chart Notation 59B) | Skin: 84 (Color Chart Notation 59D) |

TABLE 11-continued

| | |
|---|---|
| X-Section Interior Color: 04 Xylem (Core) (Color Chart Notation 59C) | Xylem: 84 (Color Chart Notation 63B) |
| X-Section Interior Color: 04 Phloem (Color Chart Notation 59C) | Phloem: 84 (Color Chart Notation 63A) |
| 7. Flower | |
| Flower Color: 86 (Color Chart Notation 193B) | Flower Color: 01 (Color Chart Notation N155D) |
| Male Fertility: Male-Sterile | Fertility: Fertile |
| Anthers: Petaloid | Anthers: Normal |
| 8. Seed | |
| Height of Seed Stalk: 92 cm | Height of Seed Stalk: 95 cm |
| Stalk Pubescence: Little | Stalk Pubescence: Little |
| Diameter of First Order Umbel: 110 mm | Diameter of First Order Umbel: 120 mm |
| Seed Spines: Present | Seed Spines: Present |
| 220 mg per 100 Seeds | 210 mg per 100 Seeds |
| 9. Disease Reaction (1 = Susceptible; 2 = Resistant; give races if known) | |
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

TABLE 12

Physiological and Morphological Characteristics of Variety RIF 71-4966C and a Comparative Variety

| RIF 71-4966C | Nutri-red |
|---|---|
| 1. Type | |
| Imperator | Red Imperator |
| 2. Region of Best Adaptation in U.S.A. | |
| Most Regions | Most Regions |
| 3. Market Maturity | |
| No. Days from Seeding to Harvest: 110 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 6 mm | Top Diameter: 30 cm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 26 cm | Leaf Blade Length: 30 cm |
| Petiole Length from Crown to First Pinna: 18 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 5 mm | Cortex Thickness: 10 mm |
| Core (Xylem) Thickness (Midpoint X-Section): 4 mm | Core Thickness: 10 mm |
| Carrot Length (Minus Taproot): 26 cm | Carrot Length: 24 cm |
| Length of Taproot: 18 mm | Length of Taproot: 20 mm |
| Diameter at Shoulder: 20 mm | Diameter at Shoulder: 32 mm |
| Diameter at Midpoint: 15 mm | Diameter at Midpoint: 22 mm |
| Amount Exposed (Above Ground): None | Amount Exposed: None |
| Shape: Cylindrical | Root Shape: Conic |
| Collar: Level | Collar: Level |
| Shoulder: Square | Shoulder: Sloping |

TABLE 12-continued

| | |
|---|---|
| Base: Medium | Base: Pointed |
| Surface Smoothness: Very Smooth | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mild Harsh | Flavor Harshness: Very harsh |
| Flavor Sweetness: Moderate Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green,
7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 182B) | 84 Shoulder (Color Chart Notation 59D) |
| Above Ground Exterior Color: 94 Skin (Color Chart Notation 182B) | Skin: 84 (Color Chart Notation 59D) |
| Below Ground Exterior Color: 94 Shoulder (Color Chart Notation 182B) | Shoulder: 84 (Color Chart Notation 59D) |
| Below Ground Exterior Color: 94 Skin (Color Chart Notation 182B) | Skin: 84 (Color Chart Notation 59D) |
| X-Section Interior Color: 04 Xylem (Core) (Color Chart Notation 182C) | Xylem: 84 (Color Chart Notation 63B) |
| X-Section Interior Color: 04 Phloem (Color Chart Notation 182C) | Phloem: 84 (Color Chart Notation 63A) |
| 7. Flower | |
| Flower Color: 01 (Color Chart Notation N155D) | Flower Color: 01 (Color Chart Notation N155D) |
| Male Fertility: Fertile | Fertility: Fertile |
| Anthers: Normal | Anthers: Normal |
| 8. Seed | |
| Height of Seed Stalk: 100 cm | Height of Seed Stalk: 95 cm |
| Stalk Pubescence: Little | Stalk Pubescence: Little |
| Diameter of First Order Umbel: 130 mm | Diameter of First Order Umbel: 120 mm |
| Seed Spines: Present | Seed Spines: Present |
| 205 mg per 100 Seeds | 210 mg per 100 Seeds |
| 9. Disease Reaction (1 = Susceptible; 2 = Resistant; give races if known) | |
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give races if known) | |
| Root knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

TABLE 13

Physiological and Morphological Characteristics of Variety RIF 71-4968B and a Comparative Variety

| RIF 71-4968B | Nutri-red |
|---|---|
| 1. Type | |
| Imperator | Red Imperator |
| 2. Region of Best Adaptation in U.S.A. | |
| Most Regions | Most Regions |
| 3. Market Maturity | |
| No. Days from Seeding to Harvest: 110 | No. Days to Market Maturity: 120 |
| 4. Plant Top (At Harvest Stage | |
| Habit: Semi-erect | Habit: Semi-erect |
| Height from Shoulder to Top of Crown: 0.5 cm | Plant Top Height: 50 cm |
| Neck Diameter: 8 mm | Top Diameter: 30 cm |
| Top Attachment: Single | Top Attachment: Single |

TABLE 13-continued

5. Leaf (At Harvest Stage)
   Name of Color Chart: RHS Colour
   Chart
   Blade Color: Dark Green                             Leaf Blade Color: Dark Green
   Color Chart Notation: N135B                         Color Chart Notation: N134A
   Blade Divisions: Medium                             Leaf Blade Divisions: Medium
   Blade Length (Without Petiole): 30 cm               Leaf Blade Length: 30 cm
   Petiole Length from Crown to First                  Leaf Petiole Length: 20 cm
   Pinna: 19 cm
   Petiole Anthocyanin: Absent                         Petiole Anthocyanin: Absent
   Petiole Pubescence: Absent                          Petiole Pubescence: Absent
6. Root (At Market Maturity)
   Cortex (Phloem) Thickness (Midpoint                 Cortex Thickness: 10 mm
   X-Section): 9 mm
   Core (Xylem) Thickness (Midpoint X-                 Core Thickness: 10 mm
   Section): 5 mm
   Carrot Length (Minus Taproot): 23 cm                Carrot Length: 24 cm
   Length of Taproot: 18 mm                            Length of Taproot: 20 mm
   Diameter at Shoulder: 25 mm                         Diameter at Shoulder: 32 mm
   Diameter at Midpoint: 20 mm                         Diameter at Midpoint: 22 mm
   Amount Exposed (Above Ground): 1-10%                Amount Exposed: None
   Shape: Conic                                        Root Shape: Conic
   Collar: Level                                       Collar: Level
   Shoulder: Rounded                                   Shoulder: Sloping
   Base: Medium                                        Base: Pointed
   Surface Smoothness: Very Smooth                     Surface Smoothness: Dimpled or Corrugated
   Number Secondary Root Scars: Few                    Secondary Root Scars: Few
   Appearance of Secondary Root Scars:                 Appearance of Secondary Roots: Prominent
   Not Prominent
   Halo: Faint                                         Halo: Faint
   Zoning: Faint                                       Zoning: Faint
   Flavor Harshness: Mild Harsh                        Flavor Harshness: Very harsh
   Flavor Sweetness: Moderate Sweet                    Flavor Sweetness: Not sweet Notes: Halo: Cross-section showing color difference between xylem and phloem.
Zoning: Longitudinal cut showing color difference between xylem kind phloem.
Color choices: 1 = White, 2 = Yellow, 3 = Orange, 4 = Red, 5 = Purple, 6 = Green,
7 = Salmon, 8 = Light, 9 = Dark
Color examples: 0 2 = Yellow; 3 4 = Orange-Red; 9 4 = Dark Red.

Colors:                                             Name of Color Chart: RHS Colour Above Ground Exterior Color: 94                     84 Shoulder (Color Chart Notation 59D)
   Shoulder (Color Chart Notation 182B)
   Above Ground Exterior Color: 94 Skin                Skin: 84 (Color Chart Notation 59D)
   (Color Chart Notation 182B)
   Below Ground Exterior Color: 94                     Shoulder: 84 (Color Chart Notation 59D)
   Shoulder (Color Chart Notation 182B)
   Below Ground Exterior Color: 94 Skin                Skin: 84 (Color Chart Notation 59D)
   (Color Chart Notation 182B)
   X-Section Interior Color: 04 Xylem                  Xylem: 84 (Color Chart Notation 63B)
   (Core) (Color Chart Notation 182C)
   X-Section Interior Color: 04 Phloem                 Phloem: 84 (Color Chart Notation 63A)
   (Color Chart Notation 182C)
7. Flower
   Flower Color: 01 (Color Chart Notation              Flower Color: 01 (Color Chart Notation N155D)
   N155D)
   Male Fertility: Fertile                             Fertility: Fertile
   Anthers: Normal                                     Anthers: Normal
8. Seed
   Height of Seed Stalk: 95 cm                         Height of Seed Stalk: 95 cm
   Stalk Pubescence: Little                            Stalk Pubescence: Little
   Diameter of First Order Umbel: 110 mm               Diameter of First Order Umbel: 120 mm
   Seed Spines: Present                                Seed Spines: Present
   200 mg per 100 Seeds                                210 mg per 100 Seeds
9. Disease Reaction (1 = Susceptible; 2 = Resistant;
   give races if known)
   *Alternaria* Blight: Susceptible                    *Alternaria* Blight: Susceptible
   *Aster* Yellows: Susceptible                        *Aster* Yellows: Susceptible
   Cavity Spot: Susceptible                            Cavity Spot: Susceptible
   *Cercospora* Blight: Susceptible
   Motley Dwarf Virus: Susceptible                     Motley Dwarf Virus: Susceptible
   Powdery Mildew: Susceptible                         Powdery Mildew: Susceptible
   *Pythium* Root Dieback: Susceptible                 *Pythium* Root Dieback: Susceptible
   *Sclerotinia* Decay: Susceptible                    *Sclerotinia* Decay: Susceptible

TABLE 13-continued

| | |
|---|---|
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

TABLE 14

Physiological and Morphological Characteristics of Variety RIF 71-4967B and a Comparative Variety

| RIF 71-4967B | Nutri-red |
|---|---|
| 1. Type | |
| Imperator | Red Imperator |
| 2. Region of Best Adaptation in U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 8 mm | Top Diameter: 30 cm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: N135B | Color Chart Notation: N134A |
| Blade Divisions: Medium | Leaf Blade Divisions: Medium |
| Blade Length (Without Petiole): 28 cm | Leaf Blade Length: 30 cm |
| Petiole Length from Crown to First Pinna: 20 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 7 mm | Cortex Thickness: 10 mm |
| Core (Xylem) Thickness (Midpoint X-Section): 4 mm | Core Thickness: 10 mm |
| Carrot Length (Minus Taproot): 25 cm | Carrot Length: 24 cm |
| Length of Taproot: 18 mm | Length of Taproot: 20 mm |
| Diameter at Shoulder: 22 mm | Diameter at Shoulder: 32 mm |
| Diameter at Midpoint: 16 mm | Diameter at Midpoint: 22 mm |
| Amount Exposed (Above Ground): None | Amount Exposed: None |
| Shape: Cylindrical | Root Shape: Conic |
| Collar: Level | Collar: Level |
| Shoulder: Rounded | Shoulder: Sloping |
| Base: Medium | Base: Pointed |
| Surface Smoothness: Very Smooth | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Mild Harsh | Flavor Harshness: Very harsh |
| Flavor Sweetness: Moderate Sweet | Flavor Sweetness: Not sweet |

Notes: Halo: Cross-section showing color difference between xylem and phloem.
Zoning: Longitudinal cut showing difference between xylem and phloem.
Color choices: 1 = White, 2 = Yellow, 3 = Orange, 4 = Red, 5 = Purple, 6 = Green, 7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 182B) | 84 Shoulder (Color Chart Notation 59D) |
| Above Ground Exterior Color: 94 Skin (Color Chart Notation 182B) | Skin: 84 (Color Chart Notation 59D) |
| Below Ground Exterior Color: 94 Shoulder (Color Chart Notation 182B) | Shoulder: 84 (Color Chart Notation 59D) |
| Below Ground Exterior Color: 94 Skin (Color Chart Notation 182B) | Skin: 84 (Color Chart Notation 59D) |

TABLE 14-continued

|  |  |
|---|---|
| X-Section Interior Color: 04 Xylem (Core) (Color Chart Notation 182C) | Xylem: 84 (Color Chart Notation 63B) |
| X-Section Interior Color: 04 Phloem (Color Chart Notation 182C) | Phloem: 84 (Color Chart Notation 63A) |
| 7. Flower | |
| Flower Color: 01 (Color Chart Notation N155D) | Flower Color: 01 (Color Chart Notation N155D) |
| Male Fertility: Fertile | Fertility: Fertile |
| Anthers: Normal | Anthers: Normal |
| 8. Seed | |
| Height of Seed Stalk: 95 cm | Height of Seed Stalk: 95 cm |
| Stalk Pubescence: Little | Stalk Pubescence: Little |
| Diameter of First Order Umbel: 115 mm | Diameter of First Order Umbel: 120 mm |
| Seed Spines: Present | Seed Spines: Present |
| 200 mg per 100 Seeds | 210 mg per 100 Seeds |
| 9. Disease Reaction (1 = Susceptible; 2 = Resistant; give races if known) | |
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Reistant) | |
| Bolting: Resistant | Bolting: Resistant |
| Root Splitting: Resistant | Root Splitting: Resistant |

TABLE 15

Physiological and Morphological Characteristics of Variety RN 71-4904C and a Comparative Variety

| RN 71-4904C | Nutri-red |
|---|---|
| 1. Type | |
| Imperator | Red Imperator |
| 2. Region of Best Adaptation in U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Semi-erect | Habit: Semi-erect |
| Height from Shoulder to Top of Crown: 0.5 cm | Plant Top Height: 50 cm |
| Neck Diameter: 10 mm | Top Diameter: 30 cm |
| Top Attachment: Single | Top Attachment: Single |
| 5. Leaf (At Harvest Stage) | |
| Name of Color Chart: RHS Colour Chart | |
| Blade Color: Medium Green | Leaf Blade Color: Dark Green |
| Color Chart Notation: N138A | Color Chart Notation: N134A |
| Blade Divisions: Medium | Leaf Blade Divisions: Medium |
| Blade Length (Without Petiole): 25 cm | Leaf Blade Length: 30 cm |
| Petiole Length from Crown to First Pinna: 20 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 8 mm | Cortex Thickness: 10 mm |
| Core (Xylem) Thickness (Midpoint X-Section): 5 mm | Core Thickness: 10 mm |
| Carrot Length (Minus Taproot): 16 cm | Carrot Length: 24 cm |
| Length of Taproot: 20 mm | Length of Taproot: 20 mm |
| Diameter at Shoulder: 25 mm | Diameter at Shoulder: 32 mm |
| Diameter at Midpoint: 22 mm | Diameter at Midpoint: 22 mm |
| Amount Exposed (Above Ground): None | Amount Exposed: None |
| Shape: Cylindrical | Root Shape: Conic |
| Collar: Level | Collar: Level |
| Shoulder: Square | Shoulder: Sloping |

TABLE 15-continued

| | |
|---|---|
| Base: Blunt | Base: Pointed |
| Surface Smoothness: Very Smooth | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Moderate to Very Harsh | Flavor Harshness: Very harsh |
| Flavor Sweetness: Not to Moderate Sweet | Flavor Sweetness: Not sweet |

Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green,
7 = Salmon, 8 = Light, 9 = Dark
Color examples: 0 2 = Yellow; 3 4 = Orange-Red; 9 4 = Dark Red.

| Colors: | Name of Color Chart: RHS Colour |
|---|---|
| Above Ground Exterior Color: 94 Shoulder (Color Chart Notation 60A) | 84 Shoulder (Color Chart Notation 59D) |
| Above Ground Exterior Color: 94 Skin (Color Chart Notation 60A) | Skin: 84 (Color Chart Notation 59D) |
| Below Ground Exterior Color: 94 Shoulder (Color Chart Notation 60A) | Shoulder: 84 (Color Chart Notation 59D) |
| Below Ground Exterior Color: 94 Skin (Color Chart Notation 60A) | Skin: 84 (Color Chart Notation 59D) |
| X-Section Interior Color: 04 Xylem (Core) (Color Chart Notation 60B) | Xylem: 84 (Color Chart Notation 63B) |
| X-Section Interior Color: 04 Phloem (Color Chart Notation 60C) | Phloem: 84 (Color Chart Notation 63A) |
| 7. Flower | |
| Flower Color: 01 (Color Chart Notation N155D) | Flower Color: 01 (Color Chart Notation N155D) |
| Male Fertility: Fertile | Fertility: Fertile |
| Anthers: Normal | Anthers: Normal |
| 8. Seed | |
| Height of Seed Stalk: 90 cm | Height of Seed Stalk: 95 cm |
| Stalk Pubescence: Little | Stalk Pubescence: Little |
| Diameter of First Order Umbel: 110 mm | Diameter of First Order Umbel: 120 mm |
| Seed Spines: Present | Seed Spines: Present |
| 190 mg per 100 Seeds | 210 mg per 100 Seeds |
| 9. Disease Reaction (1 = Susceptible; 2 = Resistant; give races if known) | |
| *Alternaria* Blight: Susceptible | *Alternaria* Blight: Susceptible |
| *Aster* Yellows: Susceptible | *Aster* Yellows: Susceptible |
| Cavity Spot: Susceptible | Cavity Spot: Susceptible |
| *Cercospora* Blight: Susceptible | |
| Motley Dwarf Virus: Susceptible | Motley Dwarf Virus: Susceptible |
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

TABLE 16

Physiological and Morphological Characteristics of Variety RN 71-4963C and a Comparative Variety

| RN 71-4963C | Nutri-red |
|---|---|
| 1. Type | |
| Nantes | Red Imperator |
| 2. Region of Best Adaptation in U.S.A. | |
| Most Regions | Most Regions |
| 3. Market Maturity | |
| No. Days from Seeding to Harvest: 120 | No. Days to Market Maturity: 120 |

TABLE 16-continued

4. Plant Top (At Harvest Stage)
   Habit: Semi-erect
   Height from Shoulder to Top of Crown: 0.5 cm
   Neck Diameter: 12 mm
   Top Attachment: Single Habit: Semi-erect
   Plant Top Height: 50 cm
   Top Diameter: 30 cm
   Top Attachment: Single 5. Leaf (At Harvest Stage)
   Name of Color Chart: RHS Colour Chart
   Blade Color: Medium Green
   Color Chart Notation: N138A
   Blade Divisions: Medium
   Blade Length (Without Petiole): 23 cm
   Petiole Length from Crown to First Pinna: 20 cm
   Petiole Anthocyanin: Absent
   Petiole Pubescence: Absent Leaf Blade Color: Dark Green
   Color Chart Notation: N134A
   Leaf Blade Divisions: Medium
   Leaf Blade Length: 30 cm
   Leaf Petiole Length: 20 cm
   Petiole Anthocyanin: Absent
   Petiole Pubescence: Absent 6. Root (At Market Maturity)
   Cortex (Phloem) Thickness (Midpoint X-Section): 9 mm
   Core (Xylem) Thickness (Midpoint X-Section): 5 mm
   Carrot Length (Minus Taproot): 16 cm
   Length of Taproot: 20 mm
   Diameter at Shoulder: 26 mm
   Diameter at Midpoint: 23 mm
   Amount Exposed (Above Ground): None
   Shape: Cylindrical
   Collar: Level
   Shoulder: Square
   Base: Blunt
   Surface Smoothness: Very Smooth
   Number Secondary Root Scars: Few
   Appearance of Secondary Root Scars: Not Prominent
   Halo: Faint
   Zoning: Faint
   Flavor Harshness: Moderate to Very Harsh
   Flavor Sweetness: Not to Moderate Sweet Cortex Thickness: 10 mm
   Core Thickness: 10 mm
   Carrot Length: 24 cm
   Length of Taproot: 20 mm
   Diameter at Shoulder: 32 mm
   Diameter at Midpoint: 22 mm
   Amount Exposed: None
   Root Shape: Conic
   Collar: Level
   Shoulder: Sloping
   Base: Pointed
   Surface Smoothness: Dimpled or Corrugated
   Secondary Root Scars: Few
   Appearance of Secondary Roots: Prominent
   Halo: Faint
   Zoning: Faint
   Flavor Harshness: Very harsh
   Flavor Sweetness: Not sweet Notes: Halo: Cross-section showing color difference between xylem and phloem.
Zoning: Longitudinal cut showing color difference between xylem and phloem.
Color choices: 1 = White, 2 = Yellow, 3 = Orange, 4 = Red, 5 = Purple, 6 = Green, 7 = Salmon, 8 = Light, 9 = Dark
Color examples: 0 2 = Yellow; 3 4 = Orange-Red; 9 4 = Dark Red.

Colors:

Above Ground Exterior Color: 94 Shoulder (Color Chart Notation 60A)
   Above Ground Exterior Color: 94 Skin (Color Chart Notation 60A)
   Below Ground Exterior Color: 94 Shoulder (Color Chart Notation 60A)
   Below Ground Exterior Color: 94 Skin (Color Chart Notation 60A)
   X-Section Interior Color: 04 Xylem (Core) (Color Chart Notation 60B)
   X-Section Interior Color: 04 Phloem (Color Chart Notation 60C)

Name of Color Chart: RHS Colour

84 Shoulder (Color Chart Notation 59D)
   Skin: 84 (Color Chart Notation 59D)
   Shoulder: 84 (Color Chart Notation 59D)
   Skin: 84 (Color Chart Notation 59D)
   Xylem: 84 (Color Chart Notation 63B)
   Phloem: 84 (Color Chart Notation 63A)

7. Flower
   Flower Color: 01 (Color Chart Notation N155D)
   Male Fertility: Fertile
   Anthers: Normal Flower Color: 01 (Color Chart Notation N155D)
   Fertility: Fertile
   Anthers: Normal 8. Seed
   Height of Seed Stalk: 100 cm
   Stalk Pubescence: Little
   Diameter of First Order Umbel: 115 mm
   Seed Spines: Present
   205 mg per 100 Seeds Height of Seed Stalk: 95 cm
   Stalk Pubescence: Little
   Diameter of First Order Umbel: 120 mm
   Seed Spines: Present
   210 mg per 100 Seeds 9. Disease Reaction (1 = Susceptible; 2 = Resistant; give races if known)
   *Alternaria* Blight: Susceptible
   *Aster* Yellows: Susceptible
   Cavity Spot: Susceptible
   *Cercospora* Blight: Susceptible
   Motley Dwarf Virus: Susceptible

*Alternaria* Blight: Susceptible
   *Aster* Yellows: Susceptible
   Cavity Spot: Susceptible Motley Dwarf Virus: Susceptible

TABLE 16-continued

| | |
|---|---|
| Powdery Mildew: Susceptible | Powdery Mildew: Susceptible |
| *Pythium* Root Dieback: Susceptible | *Pythium* Root Dieback: Susceptible |
| *Sclerotinia* Decay: Susceptible | *Sclerotinia* Decay: Susceptible |
| 10. Insect Reaction (1 = Susceptible; 2 = Resistant; give races if known) | |
| Root Knot Nematode: Susceptible | Root Knot Nematode: Susceptible |
| 11. Physiological Reaction (1 = Susceptible; 2 = Resistant) | |
| Bolting: Resistant | Bolting: Resistant |
| Root Splitting: Resistant | Root Splitting: Resistant |

TABLE 17

Physiological and Morphological Characteristics of Variety RF 71-4911A and a Comparative Variety

| RF 71-4911A | Nutri-red |
|---|---|
| 1. Type | |
| Imperator | Red Imperator |
| 2. Region of Best Adaptation U.S.A. | |
| Most Regions | Most Regions |
| 3. Market Maturity | |
| No. Days from Seeding to Harvest: 120 | No. Days to Market Maturity: 120 |
| 4. Plant Top (At Harvest Stage) | |
| Habit: Erect | Habit: Erect |
| Height from Shoulder to Top of Crown: 45 cm | Plant Top Height: 50 cm |
| Neck Diameter: 120 mm | Plant Top Diameter: 30 cm |
| Top Attachment: Single | Top Attachment: Single |
| 5. Leaf (At Harvest Stage) | |
| Name of Color Chart: RHS Colour Chart | |
| Blade Color: Dark Green | Leaf Blade Color: Dark Green |
| Color Chart Notation: 132B | Color Chart Notation: N134A |
| Blade Divisions: Medium | Leaf Blade Divisions: Medium |
| Blade Length (Without Petiole): 28 cm | Leaf Blade Length: 30 cm |
| Petiole Length from Crown to First Pinna: 18 cm | Leaf Petiole Length: 20 cm |
| Petiole Anthocyanin: Absent | Petiole Anthocyanin: Absent |
| Petiole Pubescence: Absent | Petiole Pubescence: Absent |
| 6. Root (At Market Maturity) | |
| Cortex (Phloem) Thickness (Midpoint X-Section): 18 mm | Cortex Thickness: 10 mm |
| Core (Xylem) Thickness (Midpoint X-Section): 13 mm | Core Thickness: 10 mm |
| Carrot Length (Minus Taproot): 24 cm | Carrot Length: 24 cm |
| Length of Taproot: 20 mm | Length of Taproot: 20 mm |
| Diameter at Shoulder: 36 mm | Diameter at Shoulder: 32 mm |
| Diameter at Midpoint: 31 mm | Diameter at Midpoint: 22 mm |
| Amount Exposed (Above Ground): None | Amount Exposed: None |
| Root Shape: Conic | Root Shape: Conic |
| Collar: Level | Collar: Level |
| Shoulder: Sloping | Shoulder: Sloping |
| Base: Medium | Base: Pointed |
| Surface Smoothness: Dimpled or Corrugated | Surface Smoothness: Dimpled or Corrugated |
| Number Secondary Root Scars: Few | Secondary Root Scars: Few |
| Appearance of Secondary Root Scars: Not Prominent | Appearance of Secondary Roots: Prominent |
| Halo: Faint | Halo: Faint |
| Zoning: Faint | Zoning: Faint |
| Flavor Harshness: Moderate Harsh | Flavor Harshness: Very harsh |
| Flavor Sweetness: Moderate Sweet | Flavor Sweetness: Very sweet |
| Colors: | Name of Color Chart: RHS Colour |
| Above Ground Exterior Color: 84 Shoulder (Color Chart Notation 184C) | 84 Shoulder (Color Chart Notation 59D) |
| Above Ground Exterior Color: 84 Skin (Color Chart Notation 184C) | Skin: 84 (Color Chart Notation 59D) |
| Below Ground Exterior Color: 84 Shoulder (Color Chart Notation 184C) | Shoulder: 84 (Color Chart Notation 59D) |

TABLE 17-continued

Physiological and Morphological Characteristics of Variety RF 71-4911A and a Comparative Variety

| | |
|---|---|
| Below Ground Exterior Color: 84 Skin (Color Chart Notation 184C) | Skin: 84 (Color Chart Notation 59D) |
| X-Section Interior Color: 84 Xylem (Core) (Color Chart Notation 184D) | Xylem: 84 (Color Chart Notation 63B) |
| X-Section Interior Color: 84 Phloem (Color Chart Notation 184D) | Phloem: 84 (Color Chart Notation 63A) |
| 7. Flower | |
| Flower Color: Green (Color Chart Notation 194C) | Flower Color: White (Color Chart Notation: N155D) |
| Male Fertility: Male-Sterile | Fertility: Fertile |
| Anthers: Petaloid | Anthers: Normal |
| 8. Seed | |
| Height of Seed Stalk: 125 cm | Height of Seed Stalk: 95 cm |
| Stalk Pubescence: Little | Stalk Pubescence: Little |
| Diameter of First Order Umbel: 120 mm | Diameter of First Order Umbel: 120 mm |
| Seed Spines: Present | Seed Spines: Present |
| 210 mg per 100 Seeds | 210 mg per 100 Seeds |
| 9. Disease Reaction | |
| *Alternaria* Blight: Susceptible | *Alternaria* Blight: Susceptible |
| *Aster* Yellows: Susceptible | *Aster* Yellows: Susceptible |
| | Cavity Spot: Susceptible |
| | Motley Dwarf Virus: Susceptible |
| | Powdery Mildew: Susceptible |
| | *Pythium* Root Dieback: Susceptible |
| *Sclerotinia* Decay: Susceptible | *Sclerotinia* Decay: Susceptible |
| 10. Insect Reaction | |
| Root Knot Nematode: Susceptible | Root Knot Nematode: Susceptible |
| 11. Physiological Reaction | |
| Bolting: Resistant | Bolting: Resistant |
| Root Splitting: Resistant | Root Splitting: Resistant |

C. Breeding Additional Carrot Lines

One aspect of the current invention concerns methods for crossing the carrot line RN 71-4904C, RF 71-4911A, RF 71-4912A, RIF 71-4966C, RIF 71-4967B, or RIF 71-4968B with itself or a second plant and the seeds and plants produced by such methods. These methods can be used for propagation of line RN 71-4904C, RF 71-4911A, RF 71-4912A, RIF 71-4966C, RIF 71-4967B, or RIF 71-4968B, or can be used to produce hybrid carrot seeds and the plants grown therefrom. Hybrid seeds are produced by crossing line RN 71-4904C, RF 71-4911A, RF 71-4912A, RIF 71-4966C, RIF 71-4967B, or RIF 71-4968B with second carrot parent line.

The development of new varieties using one or more starting varieties is well known in the art. In accordance with the invention, novel varieties may be created by crossing line RN 71-4904C, RF 71-4911A, RF 71-4912A, RIF 71-4966C, RIF 71-4967B, or RIF 71-4968B followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line or population, often five or more generations of selfing or sib-mating and selection are involved.

Backcrossing can also be used to improve a line. Backcrossing transfers a specific desirable trait from one line to a line lacks that trait. This can be accomplished, for example, by first crossing a superior plant (A) (recurrent parent) to a donor plant (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with RN 71-4904C, RF 71-4911A, RF 71-4912A, RIF 71-4966C, RIF 71-4967B, or RIF 71-4968B for the purpose of developing novel carrot lines, it will typically be preferred to choose those plants which either themselves exhibit one or more selected desirable characteristics or which exhibit the desired characteristic(s) when in hybrid combination. Examples of desirable characteristics may include, but are not limited to, desirable root characteristics, such as color, diameter, length, uniform taper, minimal forking, high moisture, soluble solids content, crispness, and sweetness. Additional examples of desirable characteristics may include disease tolerance, insect resistance, adaptability for soil conditions, adaptability for climate conditions, germination, seedling vigor, growth rate, maturity, plant uniformity, increased phytochemical content, increased beta-carotene content, increased xanthophyll content, increased lycopene content, and increased anthocyanin content.

As used herein, an "elite line" is any line that has resulted from breeding and selection for superior agronomic performance. An elite plant is any plant from an elite line. Examples of elite lines are lines that are commercially available to farmers or carrot breeders such as A-Plus, HCM, B8080, B6274, B5280, B6333, B5238, and B6274 (each available from the USDA).

Plants that have been self pollinated once or twice followed by sib pollination and selected for type over many generations retain some genotypic heterozygosity, but become phenotypically uniform. Such a breeding procedure is used with carrots which suffer significant inbreeding depression. A cross between two such heterozygous but homogeneous parents produces a phenotypically uniform population of hybrid plants that are heterozygous for many gene loci. The development of such parent lines generally requires at least about 5 to 7 generations of selfing and/or sib mating. Two such parent lines can then be crossed to develop improved $F_1$ hybrids. Hybrids can then be screened and evaluated in small scale field trials. Typically, about 10 to 15 phenotypic traits, selected for their potential commercial value, can be measured. In another aspect, dihaploid plants are developed and these plants are genotypically uniform. Two such plants can be crossed, or a conventionally produced parent line described above can be crossed with a dihaploid, producing $F_1$ hybrids that are evaluated as described above.

The present invention also provides progeny of high lycopene carrots. As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less genetic material derived from one of the two originally crossed plants. As used herein, a second plant is derived from a first plant if the second plant's pedigree includes the first plant.

Plants generated using a method of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using any method available, such as, marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

The present invention provides processes of preparing novel carrot plants and carrot plants produced by such processes. In accordance with such a process, a first parent carrot plant may be crossed with a second parent carrot plant wherein at least one of the first and second carrot plants is a parent line or dihaploid line or open pollinated line high lycopene carrot plant as described herein. One application of the process is in the production of $F_1$ hybrid plants. Another important aspect of this process is that the process can be used for the development of novel parent, dihaploid or open pollinated lines. For example, a high lycopene carrot plant as described herein could be crossed to any second plant, and the resulting hybrid progeny each selfed and/or sibbed for about 5 to 7 or more generations, thereby providing a large number of distinct, parent lines. These parent lines could then be crossed with other lines and the resulting hybrid progeny analyzed for beneficial characteristics. In this way, novel lines conferring desirable characteristics could be identified.

Carrot plants (*Daucus carota* var. *sativus*) can be crossed by either natural or mechanical techniques. Mechanical pollination can be effected either by controlling the types of pollen that can be transferred onto the stigma or by pollinating by hand.

In another aspect, the present invention provides a method of producing a carrot plant having an increased lycopene content comprising: (a) crossing a carrot line having increased lycopene with a second carrot line to form a segregating population; (b) screening the population for increased lycopene content; and (c) selecting one or more members of the population having increased lycopene content.

In another aspect, the present invention provides a method of introgressing a high lycopene content trait into a carrot plant comprising: (a) crossing at least a first carrot line having an increased lycopene content with a second carrot line to form a segregating population; (b) screening the population for lycopene content; and (c) selecting at least one member of the population having an increased lycopene content.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which the stigmas on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

Alternatively, in another aspect of the invention, both first and second parent carrot plants can be a high lycopene carrot plant as described herein. Thus, any carrot plant produced using a high lycopene carrot plant as described herein forms a part of the invention. As used herein, crossing can mean selfing, backcrossing, crossing to another or the same parent line, crossing to populations, and the like. All carrot plants produced using a high lycopene carrot plant as described herein as a parent are, therefore, within the scope of this invention.

In one aspect, any male carrot can be used in combination with carrots of the present invention. In one aspect, one of the parents is a male carrot having a root with a lycopene content of at least 50 ppm, 55 ppm, 60 ppm, 65 ppm, 70 ppm, 75 ppm, 80 ppm, 85 ppm, 90 ppm, 95 ppm, or 100 ppm. Examples of such male carrot lines include Nutri-red, and lines of red Indian descent carrots.

In another aspect, the present invention provides a hybrid carrot plant having an increased lycopene content. In another aspect, the present invention provides seed of a hybrid carrot plant having an increased lycopene content. Any time a high lycopene carrot plant as described herein is crossed with another, different, carrot parent line, a first generation ($F_1$) carrot hybrid plant is produced. As such, an $F_1$ hybrid carrot plant can be produced by crossing a high lycopene carrot plant, for example, as described herein with any second parent carrot plant. Essentially any other carrot plant can be used to produce a hybrid carrot plant having a high lycopene carrot plant as described herein as one parent. All that is required is that, at a minimum, one plant be female fertile and the second plant be male fertile. Carrot plants naturally are both male and female fertile.

A single cross hybrid carrot variety is the cross of two parent lines, each of which has a genotype which complements the genotype of the other. Typically, $F_1$ hybrids are more vigorous than their parents. This hybrid vigor, or heterosis, is manifested in many polygenic traits, including improved yields, better roots, better uniformity and better insect and disease resistance. In the development of hybrids only the $F_1$ hybrid plants are typically sought. An $F_1$ single cross hybrid is produced when two parent plants are crossed. A double cross hybrid is produced from four parent plants crossed in pairs (A×B and C×D) and then the two $F_1$ hybrids are crossed again (A×B)×(C×D). A three-way cross is produced from three parent plants crossed as (A×B)×C.

In one aspect, any of the carrot varieties known to those of skill in the art can be crossed with a high lycopene carrot line of the present invention to produce a hybrid plant. In a preferred aspect, such carrot varieties include, but are not limited to B3640M, B3080M, B3475, B8080, B5280, B6333, B5238, and B6274 (each available from the USDA) S-D813B (Seminis Vegetable Seeds, and U.S. Pat. No. 6,787,685, the entirety of which is incorporated herein by reference).

When a high lycopene carrot plant as described herein is crossed with another parent plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Therefore, a decision to use one parent plant as a male or female may be made based on any such characteristics as is well known to those of skill in the art.

The development of new varieties using one or more starting varieties is well known in the art. In accordance with the invention, novel varieties may be created by crossing a high lycopene carrot plant as described herein followed by multiple generations of breeding according to such well known methods. New varieties may be created by crossing a high lycopene carrot plant as described herein with any second plant. In selecting such a second plant to cross for the purpose of developing novel parent lines, it may be desired to choose those plants which either themselves exhibit one or more selected desirable characteristics or which exhibit the desired characteristic(s) when in hybrid combination. Examples of potentially desired characteristics include greater yield, resistance to insecticides, herbicides, pests, and disease, tolerance to heat and drought, reduced time to crop maturity, better agronomic quality, higher nutritional value, and uniformity in germination times, growth rate, maturity, and root size.

Once initial crosses have been made with a high lycopene carrot line of the present invention, selfing and/or sibbing take place to produce new parent lines. The development of parent lines requires manipulation by human breeders. A combination of self pollination and sib pollination is essential to develop a new parent line that is genotypically stable and phenotypically uniform. The reason for the breeder to create parent lines is to develop homogeneous populations in an outcrossing species that are phenotypically uniform and can be utilized to produce $F_1$ hybrids.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed or sibbed and selected in successive generations. Each succeeding generation becomes more genetically homogeneous and phenotypically uniform as a result of self- or sib-pollination and selection. Typically, this method of breeding involves five or more generations of selfing or sibbing and selection. After at least five generations, the resulting parent line has a stable allelic frequency at each locus and is phenotypically uniform.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, herbicide resistance, resistance for bacterial, fungal, or viral disease, insect resistance, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

D. Performance Characteristics

As described above, carrot lines RN 71-4904C, RF 71-4911A, RF 71-4912A, RIF 71-4966C, RIF 71-4967B and RIF 71-4968B, and carrot hybrid varieties 0710 0325, 0710 0339, 0710 0346, 710313, 710305, 710316, 710319, 710311, 710304, 710310, and 710303 exhibit desirable agronomic traits, including, for example, increased lycopene content. An objective analysis of the performance traits of the several of these lines and hybrid varieties relative to other lines and varieties are presented below.

Field trial results of carrot line RN 71-4904C, compared to the Nutri-red line, are shown in Tables 18-22. The values provided are obtained from averages of samples collected from about 50 roots for each variety.

TABLE 18

Performance Characteristics For Line RN 71-4904C in Year 8

|  | Nutri-red | RN 71-4904C |
| --- | --- | --- |
| Color | Red throughout | Red throughout |
| Brix (°Bx) | 9.6 | 9.8 |
| % juice | 50 | 53 |
| Lycopene (ppm) | 102.3 | 142.0 (138.8% of Nutri-Red value) |
| Anthocyanin (ppm) | 0 | 0 |
| Lutein (ppm) | 0.6 | 0.4 |
| International Units of Vitamin A/g | 60.6 | 27.7 |
| Sucrose (% g, wt/wt) | 4.1 | 4.0 |
| Glucose (% g, wt/wt) | 1.3 | 1.3 |
| Fructose (% g, wt/wt) | 1.5 | 1.1 |
| Total sugar (% g, wt/wt) | 6.8 | 6.4 |

TABLE 19

Performance Characteristics For Line RN 71-4904C in Year 9

|  | Nutri-red | RN 71-4904C |
| --- | --- | --- |
| Color | Red throughout | Red throughout |
| Brix (°Bx) | 10.1 | 9.2 |
| % Juice | n.d. | n.d. |
| Lycopene (ppm) | 78.9 | 148.7 (188.5% of Nutri-red value) |

TABLE 19-continued

Performance Characteristics For Line RN 71-4904C in Year 9

|  | Nutri-red | RN 71-4904C |
|---|---|---|
| Anthocyanin (ppm) | 0.0 | 0.0 |
| Lutein (ppm) | 0.3 | 1.5 |
| International Units of Vitamin A/g | 29.3 | 25.3 |
| Sucrose (% g, wt/wt) | 3.1 | 3.6 |
| Glucose (% g, wt/wt) | 1.2 | 0.9 |
| Fructose (% g, wt/wt) | 1.6 | 0.9 |
| Sweetness Index | 6.8 | 5.8 |
| Total sugar (% g, wt/wt) | 6.0 | 5.4 | n.d. = not determined
Sweetness Index = 1.73 * [Fructose] + 0.75 * [Glucose] + [Sucrose]

TABLE 20

Performance Characteristics For Line RN 71-4904C in Year 10

|  | Nutri-red | RN 71-4904C |
|---|---|---|
| color | Red throughout | Red throughout |
| Brix | 12.3 | 11.2 |
| % Juice | 51% | 52% |
| Lycopene (ppm) | 64.8 | 102.3 (157.9% of Nutri-red value) |
| Anthocyanin (ppm) | 0.0 | 0.0 |
| Lutein (ppm) | 0.00 | 1.07 |
| International Units of Vitamin A/g | 37.7 | 32.0 |
| Sucrose (% g, wt/wt) | 3.8 | 5.6 |
| Glucose (% g, wt/wt) | 1.1 | 0.9 |
| Fructose (% g, wt/wt) | 1.4 | 0.8 |
| Sweetness Index | 7.0 | 7.6 |
| Total sugar (% g, wt/wt) | 6.3 | 7.2 |

TABLE 21

Performance Characteristics For Line RN 71-4904C in Year 11

|  | Nutri-red | RN 71-4904C |
|---|---|---|
| Color | Red throughout | Red throughout |
| Brix | 11.36 | 10.2 |
| Juice yield (%) | 52% | 47% |
| Lycopene (ppm) | 116.86 | 199.92 (171.1% of Nutri-red value) |
| Anthocyanin (ppm) | 0.0 | 0.0 |
| Lutein (ppm) | 0.0 | 2.41 |
| International Units of Vitamin A/g | 39.54 | 53.48 |
| Sucrose (% g, wt/wt) | 2.94 | 4.25 |
| Glucose (% g, wt/wt) | 1.36 | 0.74 |
| Fructose (% g, wt/wt) | 1.49 | 0.56 |
| Sweetness index | 6.54 | 5.77 |
| Total sugar (% g, wt/wt) | 5.79 | 5.55 |

TABLE 22

Additional Performance Characteristics For Line RN 71-4904C in Year 11

|  | Nutri-red | RN 71-4904C |
|---|---|---|
| Weight (g) | 100 | 85.9 |
| % total solids (g dry matter/100 g fresh weight) | 10.37 | 12.7 |
| Nitrate (ppm) | 204.9 | 85.2 |
| Beta Carotene (ppm) | 23.72 | 32.09 |
| Alpha carotene (ppm) | 0.0 | 0.0 |
| Terpenes (ppm) (determined by HPLC) |  |  |
| Alpha-pinene | 0.914 | 0.735 |
| Beta-pinene | 3.053 | 0.865 |
| Myrcene | 0.612 | 0.908 |
| Alpha-phellandrene | 0.246 | 0.16 |
| Alpha-terpinene | 0.107 | 0.086 |
| Limonene | 1.216 | 1.096 |
| Gamma-terpinene | 3.872 | 3.304 |
| Terpinolene | 18.767 | 15.633 |
| Terpineol | 0.184 | 0.189 |
| Bornyl acetate | 0.672 | 6.446 |
| Caryophyllene | 0.482 | 12.256 |
| Bis-Abolene | 9.847 | 7.574 |
| Pike* | 28.4 | 22.5 |
| Simon** | 39.8 | 49.1 |

*Pike = Alpha-pinene, beta-pinene, myrcene, limonene, gamma-terpinene, and terpinolene.
**Simon = Alpha-pinene, beta-pinene, myrcene, limonene, gamma-terpinene, terpineol, bornyl acetate, caryophyllene, and bis-abolene.

Field trial results of carrot lines 0710 0325, 0710 0339, and 0710 0346 are shown in Table 23 below. The values provided are obtained from averages of bulked samples collected from about 20 roots for each variety.

TABLE 23

Performance Characteristics For Carrot Hybrid Varieties 0710 0325, 0710 0339, and 0710 0346

|  | Brix | Total Solids | Fructose | Glucose | Sucrose | Total Sugars | Lutein | Lycopene | Beta Carotene |
|---|---|---|---|---|---|---|---|---|---|
| Invicta | 11.0 | 12.9 | 2.01 | 2.20 | 3.00 | 7.21 | 1.58 | 00.3 | 71.3 |
| Nutri-red | 20.0 | 12.2 | 0.78 | 0.75 | 3.94 | 5.47 | 0.36 | 75.8 | 20.6 |
| Shinku Kintoki | 10.2 | 12.8 | 0.89 | 0.97 | 3.91 | 5.77 | 0.55 | 93.8 | 23.3 |
| Honkou Kintoki | 11.1 | 13.4 | 0.82 | 1.17 | 4.40 | 6.39 | 0.36 | 92.5 | 24.0 |
| 0710 0325 | 15.8 | 16.8 | 0.82 | 0.88 | 6.30 | 8.01 | 2.87 | 110.2 (145.4% of Nutri-red value) | 47.2 |

TABLE 23-continued

Performance Characteristics For Carrot Hybrid Varieties 0710 0325, 0710 0339, and 0710 0346

| | Brix | Total Solids | Fructose | Glucose | Sucrose | Total Sugars | Lutein | Lycopene | Beta Carotene |
|---|---|---|---|---|---|---|---|---|---|
| 0710 0339 | 16.0 | 14.6 | 1.43 | 1.27 | 3.75 | 6.45 | 0.0 | 100.4 (132.5% of Nutri-red value) | 24.4 |
| 0710 0346 | 13.7 | 15.9 | 1.18 | 1.12 | 5.36 | 7.67 | 0.82 | 115.3 (152.1% of Nutri-red value) | 25.1 |

Invicta, an orange (carotene) hybrid, the two Kintoki OP lines and Nutri-red were used for comparative purposes in the study summarized in Table 23. All data was obtained from Imperial Valley, Calif., February of Year 7. The tables show that hybrid 0710 0325 exhibits superior lycopene and lutein content, plus it contains a fair amount of beta-carotene, when compared to competing lines. One important aspect of the invention thus provides seed of the variety for commercial use. Also 0710 0325, 0710 0339, and 0710 0346 each exhibited higher sucrose content than the comparison varieties.

Carrot hybrid varieties 710313, 710305, 710316, 710319, 710311, 710304, 710310, and 710303 are compared in Table 24, below. The lycopene content for 50 roots from each hybrid line was analyzed by HPLC from plants grown in El Centro, Calif. Table 24 presents the average lycopene content for each of these hybrid varieties and also for control lines Honkou Kintoki, Invicta (an orange line; carotene content), Red Nantes, and Shinku Kintoki.

TABLE 24

Performance Characteristics For Carrot Hybrid Varieties 710313, 710305, 710316, 710319, 710311, 710304, 710310, and 710303

| IDC | Field | Hybrid | Count | Stats | Brix | Lycopene | Carotenes |
|---|---|---|---|---|---|---|---|
| 10325 | 971 | 71 0305 | 50 | Average | 11.50 | 117.82 | |
| | | | | Median | 10.82 | 115.80 | |
| | | | | Min | 9.01 | 93.86 | |
| | | | | Max | 17.80 | 158.25 | |
| | | | | St. dev | 1.86 | 16.29 | |
| 10327 | 977 | 71 0311 | 50 | Average | 10.23 | 119.50 | |
| | | | | Median | 10.06 | 120.01 | |
| | | | | Min | 8.97 | 90.91 | |
| | | | | Max | 12.00 | 148.10 | |
| | | | | Stdev | 0.77 | 14.75 | |
| 10329 | 979 | 71 0313 | 50 | Average | 10.97 | 127.81 | |
| | | | | Median | 10.78 | 125.48 | |
| | | | | Min | 9.07 | 97.29 | |
| | | | | Max | 13.67 | 174.15 | |
| | | | | Stdev | 1.09 | 16.86 | |
| 10331 | 982 | 71 0316 | 50 | Average | 11.44 | 118.34 | |
| | | | | Median | 11.05 | 119.96 | |
| | | | | Min | 8.79 | 82.82 | |
| | | | | Max | 17.57 | 159.71 | |
| | | | | Stdev | 1.84 | 18.18 | |
| 10333 | 985 | 71 0319 | 49 | Average | 10.15 | 89.14 | |
| | | | | Median | 10.03 | 88.51 | |
| | | | | Min | 8.85 | 59.95 | |
| | | | | Max | 11.91 | 120.71 | |
| | | | | Stdev | 0.75 | 15.38 | |
| 10343 | 6071 | Honkou Kintoki | 50 | Average | 11.18 | 98.97 | |
| | | | | Median | 10.97 | 98.88 | |
| | | | | Min | 8.77 | 62.88 | |
| | | | | Max | 17.62 | 149.93 | |
| | | | | Stdev | 1.78 | 19.97 | |
| 10339 | 208 | Invicta (comparison line) | 51 | Average | 10.18 | ND | 82.63 |
| | | | | Median | 9.98 | ND | 83.65 |
| | | | | Min | 8.50 | ND | 56.12 |
| | | | | Max | 15.36 | ND | 134.00 |
| | | | | Stdev | 1.00 | ND | 15.08 |
| 10346 | 6069 | Red Nantes (710302) | 51 | Average | 10.11 | 125.89 | |
| | | | | Median | 9.84 | 122.66 | |
| | | | | Min | 8.13 | 88.78 | |

TABLE 24-continued

Performance Characteristics For Carrot Hybrid Varieties 710313, 710305, 710316, 710319, 710311, 710304, 710310, and 710303

| IDC | Field | Hybrid | Count | Stats | Brix | Lycopene | Carotenes |
|---|---|---|---|---|---|---|---|
| | | | | Max | 16.34 | 188.10 | |
| | | | | Stdev | 1.36 | 21.97 | |
| 10344 | 6070 | Shinku Kintoki (comparison line) | 51 | Average | 10.87 | 96.77 | |
| | | | | Median | 10.61 | 94.08 | |
| | | | | Min | 7.68 | 59.88 | |
| | | | | Max | 15.84 | 146.20 | |
| | | | | Stdev | 1.49 | 21.99 | |

* ND = Non Detectable.

Four of the hybrid carrot varieties produced roots having an average lycopene content of at least about 115 ppm. Hybrid variety 710319 segregated for the red phenotype and accordingly produced a lower average lycopene content.

A performance analysis of Line RF 71-4911A was also carried out. The results of the analysis are presented below, in Tables 25 and 26.

TABLE 25

Physiological and Morphological Characteristics of Line RF 71-4911A, based on 20 root sample averages. Roots harvested from Imperial Valley, CA during February 2006 and February 2007.

| | RF 71-4911A | | Nutri-red | |
|---|---|---|---|---|
| | February, 2006 | February, 2007 | February, 2006 | February, 2007 |
| Color | Red Throughout | Red Throughout | Red Throughout | Red Throughout |
| Brix | 11.2 | 11.1 | 13.3 | 20.0 |
| Total Solids (%) | 13.6 | 12.9 | 13.4 | 12.2 |
| Beta Carotene (ppm) | 38.2 | 27.1 | 25.0 | 20.6 |
| Lycopene (ppm) | 114.7 (106.0% of Nutri-red 2006 value) | 133.6 (176.3% of Nutri-red 2007 value) | 108.2 | 75.8 |
| Lutein (ppm) | 1.5 | 0.41 | 0.49 | 0.36 |
| International Units of Vitamin A/g | 63.6 | 45.2 | 41.7 | 34.3 |
| Sucrose (% g, wt/wt) | 5.01 | 3.92 | 3.8 | 3.94 |
| Glucose (% g, wt/wt) | 1.25 | 0.68 | 0.83 | 0.75 |
| Fructose (% g, wt/wt) | 1.21 | 0.63 | 1.07 | 0.78 |
| Sweetness Index | 8.05 | 5.52 | 6.28 | 5.85 |
| Total sugar (% g, wt/wt) | 7.48 | 5.23 | 5.70 | 5.47 |
| Root Length (cm) | 24.2 | 23.0 | 25.9 | 24.7 |
| Root Diameter @ crown (cm) | 4.0 | 3.8 | 4.4 | 4.2 |

TABLE 26

Performance Characteristics For Line RF 71-4911A

| | RF71-4911A | Nutri-red | RN 71-4904C | S-D813B |
|---|---|---|---|---|
| Root Length (cm) | 24.2 | 25.9 | 16.4 | 19.3 |
| Root Diameter @ crown (cm) | 4.0 | 4.4 | 2.6 | 1.8 |
| Root Diameter @ midsection (cm) | 3.0 | 3.2 | 2.1 | 1.6 |
| Root Diameter @ root tip (cm) | 0.7 | 0.6 | 1.6 | 1.2 |
| Root Exterior Color* | 181B | 180C | 181A | 33B |
| Root Interior Phloem Color* | 180D | 179C | 179C | 32B |
| Size of Core @ midsection (mm) | 14 | 14 | 2 | 5 |
| Color of Core* | 180D | 179C | 10D | 32B |
| Color of Vascular Cambium* | 180D | 179C | 155B | 32B |
| Foliage Height (cm at 120 days) | 26 | 30 | 25 | 22 |
| Foliage Color* | 132B | 132A | 140A | N134B |

*Color ratings from the RHS Colour Chart

A performance analysis of Line RF 71-4912A was additionally carried out. The results of the analysis are presented below, in Tables 27 and 28.

TABLE 27

Physiological and Morphological Characteristics of Line RF 71-4912A, based on 20 root sample averages. Roots harvested from Imperial Valley, CA during February 2006 and February 2007.

| | RF 71-4912A | | Nutri-red | |
|---|---|---|---|---|
| | February, 2006 | February, 2007 | February, 2006 | February, 2007 |
| Color | Red Throughout | Red Throughout | Red Throughout | Red Throughout |
| Brix | 11.2 | 14.3 | 13.3 | 20.0 |
| Total Solids (%) | 13.6 | 13.5 | 13.4 | 12.2 |
| Beta Carotene (ppm) | 38.2 | 26.4 | 25.0 | 20.6 |
| Lycopene (ppm) | 114.7 (106.0% of Nutri-red 2006 value) | 85.5 (112.8% of Nutri-red 2007 value) | 108.2 | 75.8 |
| Lutein (ppm) | 1.5 | 0.13 | 0.49 | 0.36 |
| International Units of Vitamin A/g | 63.6 | 44.0 | 41.7 | 34.3 |
| Sucrose (% g, wt/wt) | 5.01 | 4.44 | 3.8 | 3.94 |
| Glucose (% g, wt/wt) | 1.25 | 0.58 | 0.83 | 0.75 |
| Fructose (% g, wt/wt) | 1.21 | 0.61 | 1.07 | 0.78 |
| Sweetness Index | 8.05 | 5.92 | 6.28 | 5.85 |
| Total sugar (% g, wt/wt) | 7.48 | "5.63 | 5.70 | 5.47 |
| Root Length (cm) | 27.3 | 26.9 | 25.9 | 24.7 |
| Root Diameter @ crown (cm) | 4.8 | 4.5 | 4.4 | 4.2 |

TABLE 28

Performance Characteristics For Line RF 71-4912A

| | RF71-4912A | Nutri-red | RN 71-4904C | S-D813B |
|---|---|---|---|---|
| Root Length (cm) | 27.3 | 25.9 | 16.4 | 19.3 |
| Root Diameter @ crown (cm) | 4.8 | 4.4 | 2.6 | 1.8 |
| Root Diameter @ midsection (cm) | 3.7 | 3.2 | 2.1 | 1.6 |
| Root Diameter @ root tip (cm) | 0.7 | 0.6 | 1.6 | 1.2 |
| Root Exterior Color* | 180A | 180C | 181A | 33B |
| Root Interior Phloem Color* | 180D | 179C | 179C | 32B |
| Size of Core @ midsection (mm) | 15 | 14 | 2 | 5 |
| Color of Core* | 180D | 179C | 10D | 32B |
| Color of Vascular Cambium* | 180D | 179C | 155B | 32B |
| Foliage Height (cm at 120 days) | 28 | 30 | 25 | 22 |
| Foliage Color* | 132B | 132A | 140A | N134B |

*Color ratings from the RHS Colour Chart

E. Further Embodiments of the Invention

When the term carrot line RN 71-4904C, RF 71-4911A, RF 71-4912A, RIF 71-4966C, RIF 71-4967B, or RIF 71-4968B is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those carrot plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental carrot plant which contributes the locus for the desired characteristic is termed the nonrecurrent or donor parent. This terminology refers to the fact that the nonrecurrent parent is used one time in the backcross protocol and therefore does not recur. The parental carrot plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a carrot plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny carrot plants of a backcross in which RN 71-4904C, RF 71-4911A, RF 71-4912A, RIF 71-4966C, RIF 71-4967B, or RIF 71-4968B is the recurrent parent comprise (i) the desired trait from the non-recurrent parent and (ii) all of the physiological and morphological characteristics of carrot line RN 71-4904C, RF 71-4911A, RF 71-4912A, RIF 71-4966C, RIF 71-4967B, or RIF 71-4968B as determined at the 5% significance level when grown in the same environmental conditions.

Carrot varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new line but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of carrot plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of carrot are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

The present application provides for carrot lines having high lycopene levels. In a preferred aspect, the carrot lines are hybrid carrot varieties. In another aspect, the present invention provides a carrot root having an increased lycopene content. Lycopene content of any of the carrot roots provided herein can be measured by any means available in the art. In one example, lycopene content of carrot roots is determined using high pressure liquid chromatography (HPLC) as described in Example 1 below. In one example, the carrot root as provided herein has a lycopene content of at least, or about 100 parts per million (ppm), 105 ppm, 110 ppm, 115 ppm, 120 ppm, 125 ppm, 130 ppm, or 135 ppm. In a preferred aspect, the carrot roots have an average lycopene content of at least about 100 ppm, 105 ppm, 110 ppm, 115 ppm, 120 ppm, 125 ppm, 130 ppm, 135 ppm, 140 ppm, 145 ppm, or 150 ppm. In another aspect, the carrot roots have an average lycopene content of between about 100 ppm and about 250 ppm, about 100 ppm and about 225 ppm, about 100 ppm and about 200 ppm, about 100 ppm and about 175 ppm, about 100 ppm and about 160 ppm, or about 100 ppm and about 150 ppm.

In another aspect, carrot lines having high lycopene content have a lycopene content that is increased at least, or greater than, 10%, 11%, 12%, 13%, 14%, 15%, 16%, 17%, 18%, 19%, 20%, 21%, 22%, 23%, 24%, 25%, 26%, 27%, 28%, 29%, or 30% relative to a control carrot line. In one embodiment, the control carrot line is Nutri-red. Nutri-red is well known variety to those of skill in the art. In specific embodiments the lycopene content of the roots of a plant provided herein may therefore be defined as comprising at least about 110% of the average root lycopene content of Nutri-red when grown under the same conditions. In further embodiments the root lycopene content may be defined as at least about 115, 120, 125, 130, 132.5, 135, 138.8, 145.4, 148.7, 152.1, 157.9, or about 171.1% of the lycopene content of Nutri-red when grown under the same conditions.

Average lycopene content of high lycopene carrot lines, as provided herein, can be determined by averaging the lycopene content of any number of roots from a line or cultivar. In one example, average lycopene content is the average of about 2, 5, 10, 15, 20, 25, 30, 35, 40, 45, or 50 roots. In a preferred aspect, the carrot plant from which the root is obtained is a male sterile plant. In another preferred aspect, the carrot plant from which the root is obtained is a cytoplasmic male sterile plant.

In another aspect, the present invention provides seed of a carrot plant capable of producing a plant having roots with a lycopene content of at least 100 ppm. In a preferred aspect, the carrot plant is grown from the seed is a male sterile plant. In another preferred aspect, the male sterile plant is a cytoplasmic male sterile plant.

The present invention also provides a cytoplasmic male sterile carrot plant having a root with an increased lycopene content.

The present invention also provides a hybrid carrot variety having a root comprising an increased lycopene content. In one example, the carrot root has an increased lycopene content of at least about 80 ppm, 85 ppm, 90 ppm, 95 ppm, 100 ppm, 105 ppm, 110 ppm, 115 ppm, 120 ppm, 125 ppm, 130 ppm, or 135 ppm. In a preferred aspect, the carrot roots have an average lycopene content of at least about 80 ppm, 85 ppm, 90 ppm, 95 ppm, 100 ppm, 105 ppm, 110 ppm, 115 ppm, 120 ppm, 125 ppm, 130 ppm, 135 ppm, 140 ppm, 145 ppm, or 150 ppm. In another aspect, the carrot roots have an average lycopene content of between about 80 ppm and about 250 ppm, about 80 ppm and about 225 ppm, about 90 ppm and about 225 ppm, about 100 ppm and about 225 ppm, about 100 ppm and about 200 ppm, about 100 ppm and about 175 ppm, or about 100 ppm and about 160 ppm, or about 100 ppm and about 150 ppm. In one embodiment, the lycopene content is measured as an average lycopene content of at least about 2, 5, 10, 15, 20, 25, 30, 35, 40, 45, 50 carrot roots obtained from the hybrid carrot variety.

In another aspect, the hybrid carrot varieties have an increased lycopene content compared to an average lycopene content obtained from a control hybrid carrot variety, for example a Kintoki open pollinated variety. For example, a carrot root obtained from a hybrid carrot of the present invention has an average lycopene content that is increased at least, or greater than, about 10%, 11%, 12%, 13%, 14%, 15%, 16%, 17%, 18%, 19%, 20%, 21%, 22%, 23%, 24%, 25%, 26%, 27%, 28%, 29%, or 30% compared to a root obtained from a control carrot line.

In another aspect, the present invention provides a carrot having a root having a color corresponding to a color in the 184 color group on the Royal Horticultural Society Color Chart (Royal Horticultural Society Publications, London, UK). In a preferred aspect, the root has a color in the 184 color group between colors RHS 184 A and RHS 184C. In a preferred aspect, the root has a color between RHS 184A and RHS 184B. In one aspect, the root has a color between RHS 184A and RHS 184C to a depth below the root surface of about, or at least 1, 2, 3, 4, 5, 6, 7, 8, 9, or 10 millimeters (mm). The depth of color is measured by measuring the color of the root from the surface to the deepest point of color.

In another aspect, the present invention provides a high lycopene carrot plant having commercially desirable root quality traits, such as crispness and sweetness, while minimizing other traits, such as forking. A review of these traits is found in "Domestication, Historical Development, and Modern Breeding of Carrot," P. W. Simon, *Plant Breeding Reviews,* 19:157-190 (ed. J. Janick; John Wiley & Sons 2000). "Crispness" of carrot roots is defined as the fracture of the root after applying a given force. "Sweetness" is the result of a carrot root's sugar content, which can, for example, be measured as soluble solids by refractometer, and expressed as degrees brix. In one aspect, a carrot plant of the present invention produces a root having a brix content of about or greater than 4°, 5°, 6°, 7°, 8°, 9°, 10°, 11°, 12°, 13°, 14°, 15°, 16°, 17°, 18° brix. In another aspect, a carrot plant of the present invention produces a root having between about 2° and about 20° brix, between about 3° and about 20° brix, between about 8° and about 20° brix, or between about 11° brix and about 20° brix.

"Forking" can occur when carrots are grown in hard clay soil, are grown in rocky soil, or are grown in crowded conditions, or due to excessive nitrogen presence, or due to various pathogens, and results in growth of secondary roots from the primary tap root. In one aspect, a population of roots of carrot lines of the present invention have less than 25%, 20%, 15%, 10%, 5% forking. Crispness, forking, and sweetness can be measured by any method known in the art. For example, crispness, sweetness, and forking may be measured by comparison of a test root to a reference standard carrot root grown under similar conditions.

In an aspect, a carrot of the present invention has a root having a diameter at harvest of about or greater than 12 millimeters (mm), 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, or 51 mm. In another aspect, a carrot has a root having a diameter at harvest between about 10 mm and about 55 mm, between about 12 mm and about 53 mm, between about 15 mm and about 50 mm, or between about 17 mm and about 48 mm. As used herein, root diameter at harvest is measured by measuring the diameter of the root at its widest point.

In an aspect, a carrot of the present invention has a root length at harvest of about or greater than 7.5 centimeters (cm), 8.0 cm, 8.5 cm, 9.0 cm, 9.5 cm, 10.0 cm, 10.5 cm, 11.0 cm, 11.5 cm, 12.0 cm, 12.5 cm, 13.0 cm, 13.5 cm, 14.0 cm, 14.5 cm, 15.0 cm, 20 cm, 25 cm, 30 cm, 35 cm, or 40 cm. In another aspect, a carrot of the present invention has a root length at harvest between about 5 cm and about 40 cm, between about 7.5 cm and about 35 cm, or between about 9 cm and about 30 cm. Root length is measured at the longest point of the root from top to bottom in centimeters. As used herein, root length is measured by measuring the harvest root along the length of the root between the greatest points.

In an aspect, a carrot root has an overall root quality rating of 1, 2, 3, 4, or 5, where root quality is measured by visual inspection, with a scale ranging from 1=poor through 5=excellent.

A carrot attribute such as color, root length, and root lycopene content can be measured at a variety of times. In another aspect, an attribute is measured following growth in a growth chamber. In one aspect, an attribute is measured at the time of harvest. In another aspect, an attribute is measured after storage of the carrot root at ambient conditions for one day, two days, three days, four days, five days, six days, one week, two weeks, three weeks, four weeks, or five weeks after harvest. In yet another aspect, an attribute is measured after storage of the carrot root at 5° C. for one day, two days, three days, four days, five days, six days, one week, two weeks, three weeks, four weeks, or five weeks.

As used herein, a carrot plant exhibits "favorable root characteristics" if the root has a diameter of between about 20 to about 50 millimeters (mm) and a length between about 50 to about 500 mm, and has a minimal amount of forking and a minimal core. In one aspect, a carrot plant demonstrates less than 25%, 20%, 15%, 10%, or 5% of its carrots having forked roots. In another aspect, a carrot root demonstrates a cortex diameter that is less than 60%, 55%, 50%, 45%, or 40% of the diameter of the total diameter of the root. In another aspect, a carrot root that has a discernable "sweetness" refers to the sensory perception of sweetness of the carrot root. In one aspect, sweetness can be correlated to the content of soluble solids in the carrot root. Soluble solids of a root can be measured as degrees brix by refractometry, and preferably is at least 4°, 6°, 8°, 10°, 12°, 14°, 16°, 18°, 20° brix or greater. Sweetness can also be affected by the amount of terpenoids, such as Pike or Simon terpenes, produced in the carrot root. Terpene content can be measured using any method available in the art, for example, using HPLC. Preferably, the root contains less than 50 ppm, 45 ppm, 40 ppm, 35 ppm, 30 ppm of terpenoids.

A further aspect of the invention relates to tissue cultures of the carrot lines described herein. As used herein, the term "tissue culture" indicates a composition comprising isolated cells of the same or a different type or a collection of such cells organized into parts of a plant. Exemplary types of tissue cultures are protoplasts, calli, anther cultures, and plant cells that are intact in plants or parts of plants, such as embryo, leaf, peduncle, pedicel, anther, meristem, tip and segments of root, stump and stem, explants, and the like. In a preferred aspect, the tissue culture comprises embryos, protoplasts, meristematic cells, pollen, leaves or anthers derived from immature tissues of these plant parts. In another preferred aspect, tissue cultures can be used in dihaploid production. Means for preparing and maintaining plant tissue cultures are well known in the art. Examples of processes of tissue culturing and regeneration of carrot are described in, for example, Matthysse et al. (1978).

As used herein, a "high lycopene" carrot line is any carrot root from a carrot line in which a population of roots having an average lycopene content of at least about 100 parts per million (ppm). In other aspects, a population of roots have an average lycopene content of at least, or greater than, about 110 ppm, 115 ppm, 120 ppm, 125 ppm, 130 ppm, 135 ppm, 140 ppm or higher. High lycopene carrot lines have an average lycopene content in a population of carrot roots of the present invention that is higher than previously described carrot plants, for example, carrot lines Indian Red and Nutri-red. A population of carrot roots refers to two or more roots obtained from different carrot plants within the same carrot line, preferably 2, 5, 10, 15, 20, 25, 30, 35, 40, 45, 50, 100, 200, 500, or 1000 or more roots, obtained from different carrot plants within the same carrot line, grown under similar conditions. In one aspect, average lycopene content is identified as an average lycopene content between about 100 ppm and about 250 ppm, between about 100 ppm and about 225 ppm, between about 100 ppm and about 200 ppm, between about 100 ppm and about 175 ppm, between about 100 ppm and about 165 ppm, or between about 100 ppm and about 155 ppm. In one aspect, the lycopene content of a carrot root is measured at harvest.

The present invention also provides a container of carrot seeds in which roots grown from greater than 50% of the seeds have an increased lycopene content. In another aspect, roots obtained from carrot plants grown from greater than 55%, 60%, 65%, 70%, 75%, 80%, 85%, 90%, 95% of the carrot seeds in the container have an increased lycopene content. In one aspect, a population of roots obtained from plants grown from the seeds have an average lycopene content between about 100 ppm and about 250 ppm, between about 100 ppm and about 225 ppm, between about 100 ppm and about 200 ppm, between about 100 ppm and about 175 ppm, between about 100 ppm and about 165 ppm, about 100 ppm and about 155 ppm, about 110 ppm and about 225 ppm, about 120 ppm and about 225 ppm, or about 125 ppm and about 225 ppm. In other aspects, a population of roots obtained from plants grown from the seeds have an average lycopene content of least, or greater than, about 100 ppm, 110 ppm, 115 ppm, 120 ppm, 125 ppm, 130 ppm, 135 ppm, 140 ppm. In this regard, the population of roots contains at least about 2, 5, 10, 15, 20, 25, 30, 35, 40, 45, 50, 100, 200, 500, or 1000 or more roots.

The container of carrot seeds can contain any number, weight or volume of seeds. For example, a container can contain at least, or greater than, about 10, 25, 50, 100, 200, 300, 400, 500, 600, 700, 800, 900, 1000, 1500, 2000, 2500, 3000, 3500, 4000 5000, 10,000, 20,000, 30,000, 40,000, 50,000 seeds. In another aspect, a container can contain about, or greater than about, 1 gram, 5, 10, 15, 20, 25, 50, 100, 250, 500, 1000 grams of seeds. Alternatively, the container can contain at least, or greater than, about 1 ounce, 5 ounces, 10 ounces, 1, 2, 3, 4, 5, 10, 15, 20, 25, 50 pounds or more seeds.

Containers of carrot seeds can be any container available in the art. For example, a container can be a box, a bag, a can, a packet, a pouch, a tape roll, a pail, or a tube.

In another aspect, the seeds contained in the containers of carrot seeds can be treated or untreated carrot seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to pelleting, film coating, and encrustments.

In another aspect, the present invention provides a container of carrot roots having at least a portion of the carrots with an increased lycopene content. In one aspect, the container contains about 2, 5, 10, 15, 20, 25, 30, 35, 40, 45, 50, 55, 60, 65, 70, 75, 80, 85, 90, 95, 100, or more carrot roots. In yet another aspect, the present invention provides a bunch of carrot roots having at least a portion of the carrots in the bunch have an increased lycopene content. In one aspect, the bunch contains about 2, 3, 4, 5, 6, 7, 8, 9, 10, 11, 12, 13, 14, 15, 16, 17, 18, 19, 20, or more carrot roots bound together. In another aspect, the present invention provides a container of cut carrot roots, such as cuts or coins, having at least a portion of the cut carrot roots having an increased lycopene content. In one aspect, the container contains about 2, 5, 10, 15, 20, 25, 30, 35, 40, 45, 50, 55, 60, 65, 70, 75, 80, 85, 90, 95, 100, or more cut carrot roots. In another aspect, the container contains 0.5 pounds, 1 pound, 2, 3, 4, 5, or more pounds of cut carrot roots. In another aspect, the container contains 5, 10, 25, 50, 75, 100, 250, 500, 1000, 2000 or more grams of cut carrot roots. The lycopene content can be measured by any means available in the art. For example, the lycopene content can be measured by averaging the lycopene content of a population of carrot roots. In this regard, a population of carrot roots can be 2, 5, 10, 15, 20, 25, 30, 35, 40, 45, 50, or more roots. Average lycopene content in the population can be between about 100 ppm and about 250 ppm, between about 100 ppm and about 225 ppm, between about 100 ppm and about 200 ppm, between about 100 ppm and about 175 ppm, between about 100 ppm and about 165 ppm, or between about 100 ppm and about 155 ppm.

In one aspect, the containers or bunches of carrots can be found in a market. For example, the containers or bunches can be found in a grocery store, a restaurant, bakery, and the like. In one aspect, the containers or bunches of carrots can be found available for sale in a market.

In another aspect, greater than 55%, 60%, 65%, 70%, 75%, 80%, 85%, 90%, 95% of the carrot roots in the container have an increased lycopene content.

Also provided herein are containers of cleaned carrot roots having an increased lycopene content. The present invention also provides a container of cleaned carrot root parts. In one aspect, a container of root parts can be sold or available for sale in a market.

F. Carrot Plants Derived by Genetic Engineering

Many useful traits that can be introduced by backcrossing, as well as directly into a plant, are those which are introduced by genetic transformation techniques. Genetic transformation may therefore be used to insert a selected transgene into the carrot line of the invention or may, alternatively, be used for the preparation of transgenes which can be introduced by backcrossing. Methods for the transformation of plants, including carrot, are well known to those of skill in the art. Techniques which may be employed for the genetic transformation of carrot include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or NYTEX screen, onto a surface covered with target carrot cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for carrot plant gene expression include, but are not limited to, the cauliflower mosaic virus (CaMV) P-35S promoter, which confers constitutive, high-level expression in most plant tissues (see, e.g., Odell et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the carrot lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a carrot plant according to the invention. Non-limiting examples of particular genes and corresponding phenotypes one may choose to introduce into a carrot plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

Many useful traits are those which are introduced by genetic transformation techniques. Methods for the genetic transformation of carrot are known to those of skill in the art. For example, methods which have been described for the genetic transformation of carrot may include electroporation, electrotransformation, microprojectile bombardment, *Agrobacterium*-mediated transformation, direct DNA uptake transformation of protoplasts and silicon carbide fiber-mediated transformation. See, e.g., Khachatourians, G., et al., eds., Transgenic Plants and Crops, Marcel Dekker, Inc. (2002).

It is understood to those of skill in the art that a transgene need not be directly transformed into a plant, as techniques for the production of stably transformed carrot plants that pass single loci to progeny by Mendelian inheritance is well known in the art. Such loci may therefore be passed from parent plant to progeny plants by standard plant breeding techniques that are well known in the art. Examples of traits that may be introduced into a carrot plant according to the invention include, for example, male sterility, herbicide resistance, disease resistance, insect resistance, and enhanced nutritional quality.

PCR and Southern hybridization are two examples of molecular techniques that can be used for confirmation of the presence of a given locus and thus conversion of that locus.

Every reference, patent, or other published work cited above is herein incorporated by reference in its entirety.

G. Determination of Lycopene Content

For lycopene analysis of individual roots, individual root tips are diced, weighed and then ground to a fine slurry with an equal weight of R/O water. A sub-sample (about 1 gram) is weighed out into an amber extraction vial. An extraction mixture of acetone, methanol and hexane is added to the vial. The carotenoids are extracted by grinding with an IKA T25 Ultra-Turrax homogenizer. The hexane is separated from the other solvents by the addition of 1 M sodium chloride solution followed by centrifugation. The lycopene is measured by transferring the hexane phase to a cuvette and reading the absorbance at 503 nm on a Cary 1 spectrophotometer (Varian, Inc., Palo Alto, Calif.).

For bulk root analyses of lycopene content, fifteen to twenty carrots are diced, weighed then ground to a fine slurry with an equal weight of R/O water. A sub-sample (about 1 gram) is weighed out into an amber extraction vial. An extraction mixture of acetone, methanol and hexane are added to the vial. The carotenoids are extracted by grinding with an IKA T25 Ultra-Turrax homogenizer. The hexane is separated from the other solvents by the addition of 1 M sodium chloride solution followed by centrifugation. The lycopene is measure by analyzing the hexane phase on an Agilent 1100 HPLC system. Fifteen micro-liters of hexane extract were injected onto a Whatman Partisil 50DS-3 WVS column and separated using an isocratic solvent mix of acetonitrile, methanol, isopropanol, water (765, 90, 162, 36). Lycopene was quantified using an Agilent G1315B diode array detector (Agilent/Hewlett Packard) at 503 nm.

H. Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in co-dominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a carrot variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a carrot plant by transformation.

Triploid: A cell or organism having three sets of chromosomes.

As used herein, a "control" carrot is a carrot line selected from the group consisting of Honkou Kintoki, Invicta, and Shinku Kintoki. In a preferred aspect, Honkou Kintoki is the control carrot line. A control carrot line is also grown under similar environmental conditions to the carrot line according to the present disclosure.

As used herein, "open-pollinated" refers to plants capable of breeding from a mixture of self and cross pollination. For example, open-pollinated plants are capable of self- or sib-pollinating and cross-pollinating.

As used herein, "cytoplasmic male sterility" refers to plants that are not capable of setting seed from self or sib pollination, but are capable of breeding from cross-pollination, due to the inability of the plant to produce pollen.

As used herein, "linkage" is a phenomenon wherein alleles on the same chromosome tend to segregate together more often than expected by chance if their transmission were independent.

As used herein, "Nantes" refers to one of the primary carrot varieties grown worldwide. The Nantes variety is generally characterized as a carrot line having sparse foliage that is weakly attached to the crown. The Nantes root is moderately long (between about 6-7 inches, or about 15 cm-18 cm) with a uniform diameter (between about 1-2 inches, or about 2.5 cm-5 cm) along its length. The root further has a rounded tip at maturity, and has a highly pigmented core, which has relatively succulent, brittle roots. The Nantes root also matures early (between about 55 days and about 100 days after sowing), and the roots are higher in sugars, but lower than average in terpenoids and dry matter making the roots less suitable for long-term storage. In addition, the surface of the root is thinner than many other varieties and scars easily.

As used herein, "red male carrot" refers to a carrot plant having an increased lycopene content that provides a source of pollen for fertilizing a female recipient carrot plant.

As used herein, an "orange male carrot" refers to a carrot plant having a root containing low or non-detectable levels of lycopene that provides a source of pollen for fertilizing a female recipient carrot plant. For example, orange male carrots produce roots having less than about 40 ppm, 30 ppm, 20 ppm, or 10 ppm lycopene. Examples of orange male carrot lines include S-D813B (Seminis Vegetable Seeds, Inc.), B3640M, B3080M, B3475, B8080, B5280, B6333, B5238, and B6274 (each available from the USDA).

As used herein, a "female parent" refers to a carrot plant that is the recipient of pollen from a male donor line. A female parent can be any carrot plant that is the recipient of pollen. Such female parents can be male sterile, for example, as a result of cytoplasmic male sterility. Cytoplasmic male sterility can be of the brown anther type, in which the anthers degenerate and shrivel prior to anthesis, and is based on S-cytoplasm and at least two recessive genes with complementary action. Cytoplasmic male sterility can also be of the petaloid type, in which five additional petals replace anthers, resulting from S-cytoplasm and at least two dominant genes with complementary action.

As used herein, a "marker" is an indicator for the presence of at least one phenotype or polymorphism, such as single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), or random amplified polymorphic DNA (RAPDs). A marker is preferably inherited in co-dominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both.

H. Deposit Information

A deposit has been made for carrot lines disclosed above and recited in the claims with the American Type Culture Collection (ATCC), 10801 University Blvd., Manassas, Va. 20110-2209. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the enforceable life of the patent, whichever is longer, and will be replaced if necessary during that period Seed samples obtained from carrot hybrid varieties were deposited under ATCC accession numbers as follows: Seeds of hybrid carrot variety 710313 (D. carotae SVR 0710 0313) were deposited under ATCC Accession No. PTA-7904 (Deposited on Oct. 4, 2006); seeds of hybrid carrot variety 710311 (D. carotae SVR 0710 0311) were deposited under ATCC Accession No. PTA-7907 (Deposited on Oct. 4, 2006); seeds of hybrid carrot variety 710319 (D. carotae SVR 0710 0319) were deposited under ATCC Accession No. PTA-7906 (Deposited on Oct. 4, 2006); seeds of hybrid carrot variety 710316 (D. carotae SVR 0710 0316) were deposited under ATCC Accession No. PTA-7905 (Deposited on Oct. 4, 2006); and seeds of carrot line 710305 (D. carotae SVR 0710 0305) were deposited under ATCC Accession No. PTA-7908 (Deposited on Oct. 4, 2006). Seeds of hybrid carrot variety 710304 (D. carotae SVR 0710 0304) were deposited under ATCC Accession No. PTA-8121 (Deposited on Jan. 10, 2007); seeds of hybrid carrot variety 710310 (D. carotae SVR 0710 0310) were deposited under ATCC Accession No. PTA-8122 (Deposited on Jan. 10, 2007); seeds of hybrid carrot variety 710303 (D. carotae SVR 0710 0303) were deposited under ATCC Accession No. PTA-8123 (Deposited on Jan. 10, 2007); seeds of carrot line RN 71-4904C (also having the designation 71 0302) were deposited under ATCC Accession No. PTA-8648 (Deposited on Sep. 25, 2007); seeds of carrot line RF 71-4911A were deposited under ATCC Accession No. PTA-8642 (Deposited on Sep. 21, 2007); seeds of carrot line RF 71-4912A were deposited under ATCC Accession No. PTA-8646 (Deposited on Sep. 21, 2007); seeds of carrot line RIF 71-4966C were deposited under ATCC Accession No. PTA-8651 (Deposited on Sep. 25, 2007); seeds of carrot line RIF 71-4967B were deposited under ATCC Accession No. PTA-8650 (Deposited on Sep. 25, 2007); seeds of carrot line RIF 71-4968B were deposited under ATCC Accession No. PTA-8649 (Deposited on Sep. 25, 2007); seeds of carrot line RN 71-4963C were deposited under ATCC Accession No. PTA-8647 (Deposited on Sep. 25, 2007); seeds of hybrid carrot variety 0710 0325 (D. carotae SVR 0710 0325) were deposited under ATCC Accession No. PTA-8643 (Deposited on Sep. 21, 2007); seeds of hybrid carrot variety 0710 0339 (D. carotae SVR 0710 0339) were deposited under ATCC Accession No. PTA-8645 (Deposited on Sep. 21, 2007); and seeds of hybrid carrot variety 0710 0346 (D. carotae SVR 0710 0346) were deposited under ATCC Accession No. PTA-8644 (Deposited on Sep. 21, 2007).

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
WO 99/31248
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Hanschke and Gabelman, *Proc. Amer. Soc. Hort. Sci.*, 82:341-350, 1963.
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Matthysse et al., *Infect. Immunol.* 22:516-522, 1978.
Nothnagel, *Plant Breeding*, 109:67-74 1992.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Stein and Nothnagel, *Plant Breeding*, 114:1-11, 1995.
Terada and Shimamoto, *Mol. Gen. Genet.*, 220:389, 1990.
Thompson, *Proc. Amer. Soc. Hort. Sci.*, 78:332-338, 1961.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.

What is claimed is:

1. A carrot plant, the roots of which comprise an average lycopene content from about 110 ppm to about 250 ppm and an average brix content from about 11° brix to about 20° brix, wherein the lycopene content of the plant is at least about 110% of the average lycopene content of roots of the carrot variety Nutri-red when the plant and Nutri-red are grown under the same conditions, and wherein said carrot plant comprises the genetic source for expressing the lycopene content in a carrot variety selected from the group consisting of red carrot hybrid 0710 0325, a sample of the seed of which has been deposited under ATCC Accession No. PTA-8643; red carrot hybrid 0710 0339, a sample of the seed of which has been deposited under ATCC Accession No. PTA-8644; red carrot hybrid 0710 0346, a sample of the seed of which has been deposited under ATCC Accession No. PTA-8645; red carrot hybrid 710313, a sample of the seed of which has been deposited under ATCC Accession No. PTA-7904; red carrot hybrid 710305, a sample of the seed of which has been deposited under ATCC Accession No. PTA-7908; red carrot hybrid 710316, a sample of the seed of which has been deposited under ATCC Accession No. PTA-7905; red carrot hybrid 710319, a sample of the seed of which has been deposited under ATCC Accession No. PTA-7906; red carrot hybrid 710311, a sample of the seed of which has been deposited under ATCC Accession No. PTA-7907; red carrot hybrid 710304, a sample of the seed of which has been deposited under ATCC Accession No. PTA-8121; red carrot hybrid 710310, a sample of the seed of which has been deposited under ATCC Accession No. PTA-8122; and red carrot hybrid 710303, a sample of the seed of which has been deposited under ATCC Accession No. PTA-8123; line RN 71-4963C, a sample of the seed of which has been ATCC Accession No. PTA-8647; line RN 71-4904C, a sample of the seed of which has been deposited under ATCC Accession No. PTA-8648; line RF 71-4911A, a sample of the seed of which has been deposited under ATCC Accession No. PTA-8642; line RF 71-4912A, a sample of the seed of which has been deposited under ATCC Accession No. PTA-8646; line RIF 71-4966C, a sample of the seed of which has been deposited under ATCC Accession No. PTA-8651; line RIF 71-4967B, a sample of the seed of which has been deposited under ATCC Accession No. PTA-8650; and line RIF 71-4968B, a sample of the seed of which has been deposited under ATCC Accession No. PTA-8649.

2. The plant of claim 1, the roots of which exhibit an average lycopene content from about 110 ppm to about 175 ppm or from about 110 ppm to about 160 ppm.

3. The plant of claim 1, the roots of which exhibit an average lycopene content that is at least about 115%, 120%, or 130% of the average lycopene content of carrot variety Nutri-red.

4. The plant of claim 1, further comprising resistance to root splitting or bolting.

5. A container of carrot roots-of the plant of claim 1, wherein the roots comprise an average lycopene content of between about 110 ppm and about 250 ppm and an average brix content of between about 12° brix and about 20° brix.

6. The container of carrot roots of claim 5, wherein said container comprises at least 100 roots.

7. The container of carrot roots of claim 5, wherein said container is selected from the group consisting of a bag, a box, a packet, a pouch, a can, and a pail.

8. The container of carrot roots of claim 5, wherein greater than 75%, 85% or 95% of said roots have said lycopene content.

9. A carrot seed capable of producing the plant of claim 1.

10. A container of carrot seeds according to claim 9, wherein said seeds are obtained from a cross between a cytoplasmic male sterile parental carrot and a male parent.

11. The container of carrot seeds of claim 10, wherein said seeds are hybrid carrot seeds.

12. The plant of claim 1, further defined as plant of a hybrid variety selected from the group consisting of red carrot hybrid 0710 0325, a sample of the seed of which has been deposited under ATCC Accession No. PTA-8643; red carrot hybrid 0710 0339, a sample of the seed of which has been deposited under ATCC Accession No. PTA-8644; red carrot hybrid 0710 0346, a sample of the seed of which has been deposited under ATCC Accession No. PTA-8645; red carrot hybrid 710313, a sample of the seed of which has been deposited under ATCC Accession No. PTA-7904; red carrot hybrid 710305, a sample of the seed of which has been deposited under ATCC Accession No. PTA-7908; red carrot hybrid 710316, a sample of the seed of which has been deposited under ATCC Accession No. PTA-7905; red carrot hybrid 710319, a sample of the seed of which has been deposited under ATCC Accession No. PTA-7906; red carrot hybrid 710311, a sample of the seed of which has been deposited under ATCC Accession No. PTA-7907; red carrot hybrid 710304, a sample of the seed of which has been deposited under ATCC Accession No. PTA-8121; red carrot hybrid 710310, a sample of the seed of which has been deposited under ATCC Accession No. PTA-8122; and red carrot hybrid 710303, a sample of the seed of which has been deposited under ATCC Accession No. PTA-8123.

13. A seed of the plant of claim 1.

14. The plant of claim 1, wherein the plant is a plant of a variety selected from the group consisting of red carrot hybrid 0710 0325, a sample of the seed of which has been deposited under ATCC Accession No. PTA-8643; red carrot hybrid 0710 0339, a sample of the seed of which has been deposited under ATCC Accession No. PTA-8644; red carrot hybrid 0710 0346, a sample of the seed of which has been deposited under ATCC Accession No. PTA-8645; red carrot hybrid 710313, a sample of the seed of which has been deposited under ATCC Accession No. PTA-7904; red carrot hybrid 710305, a sample of the seed of which has been deposited under ATCC Accession No. PTA-7908; red carrot hybrid 710316, a sample of the seed of which has been deposited under ATCC Accession No. PTA-7905; red carrot hybrid 710319, a sample of the seed of which has been deposited under ATCC Accession No. PTA-7906; red carrot hybrid 710311, a sample of the seed of which has been deposited under ATCC Accession No. PTA-7907; red carrot hybrid 710304, a sample of the seed of which has been deposited under ATCC Accession No. PTA-8121; red carrot hybrid 710310, a sample of the seed of which has been deposited under ATCC Accession No. PTA-8122; and red carrot hybrid 710303, a sample of the seed of which has been deposited under ATCC Accession No. PTA-8123; line RN 71-4963C, a sample of the seed of which has been ATCC Accession No. PTA-8647; line RN 71-4904C, a sample of the seed of which has been deposited under ATCC Accession No. PTA-8648; line RF 71-4911A, a sample of the seed of which has been deposited under ATCC Accession No. PTA-8642; line RF 71-4912A, a sample of the seed of which has been deposited under ATCC Accession No. PTA-8646; line RIF 71-4966C, a sample of the seed of which has been deposited under ATCC Accession No. PTA-8651; line RIF 71-4967B, a sample of the seed of which has been deposited under ATCC Accession No. PTA-8650; and line RIF 71-4968B, a sample of the seed of which has been deposited under ATCC Accession No. PTA-8649.

15. The seed of claim 9, wherein the seed is of a variety selected from the group consisting of red carrot hybrid 0710 0325, a sample of the seed of which has been deposited under ATCC Accession No. PTA-8643; red carrot hybrid 0710 0339, a sample of the seed of which has been deposited under ATCC Accession No. PTA-8644; red carrot hybrid 0710 0346, a sample of the seed of which has been deposited under ATCC Accession No. PTA-8645; red carrot hybrid 710313, a sample of the seed of which has been deposited under ATCC Accession No. PTA-7904; red carrot hybrid 710305, a sample of the seed of which has been deposited under ATCC Accession No. PTA-7908; red carrot hybrid 710316, a sample of the seed of which has been deposited under ATCC Accession No. PTA-7905; red carrot hybrid 710319, a sample of the seed of which has been deposited under ATCC Accession No. PTA-7906; red carrot hybrid 710311, a sample of the seed of which has been deposited under ATCC Accession No. PTA-7907; red carrot hybrid 710304, a sample of the seed of which has been deposited under ATCC Accession No. PTA-8121; red carrot hybrid 710310, a sample of the seed of which has been deposited under ATCC Accession No. PTA-8122; and red carrot hybrid 710303, a sample of the seed of which has been deposited under ATCC Accession No. PTA-8123; line RN 71-4963C, a sample of the seed of which has been ATCC Accession No. PTA-8647; line RN 71-4904C, a sample of the seed of which has been deposited under ATCC Accession No. PTA-8648; line RF 71-4911A, a sample of the seed of which has been deposited under ATCC Accession No. PTA-8642; line RF 71-4912A, a sample of the seed of which has been deposited under ATCC Accession No. PTA-8646; line RIF 71-4966C, a sample of the seed of which has been deposited under ATCC Accession No. PTA-8651; line RIF 71-4967B, a sample of the seed of which has been deposited under ATCC Accession No. PTA-8650; and line RIF 71-4968B, a sample of the seed of which has been deposited under ATCC Accession No. PTA-8649.

* * * * *